United States Patent [19]
Jennings-White et al.

[11] Patent Number: 5,792,757
[45] Date of Patent: Aug. 11, 1998

[54] 19-NOR-PREGNANE STEROIDS AS NEUROCHEMICAL INITIATORS OF CHANGE IN HUMAN HYPOTHALAMIC FUNCTION

[75] Inventors: Clive L. Jennings-White, Salt Lake City, Utah; David L. Berliner, Atherton, Calif.; Nathan William Adams, Salt Lake City, Utah

[73] Assignee: Pherin Pharmaceuticals, Menlo Park, Calif.

[21] Appl. No.: 485,615

[22] Filed: Jun. 7, 1995

Related U.S. Application Data

[63] Continuation-in-part of Ser. No. 286,073, Aug. 4, 1994, Pat. No. 5,563,131.

[51] Int. Cl.$^6$ ..................... A61K 31/56
[52] U.S. Cl. ............ 514/170; 514/177; 514/178; 514/181; 514/182; 552/558
[58] Field of Search ............... 514/182, 170, 514/177, 178, 181; 552/558

[56] References Cited

U.S. PATENT DOCUMENTS

| | | | |
|---|---|---|---|
| 5,108,994 | 4/1992 | Casper | 514/170 |
| 5,272,134 | 12/1993 | Berliner | 512/3 |
| 5,278,141 | 1/1994 | Berliner | 512/3 |

OTHER PUBLICATIONS

Hsia et al., "Inhibition of Glucuronosyl Transferase by Steroid Hormones", *Archives of Biochemistry and Biophysics*, 103:181–185 (1963).

Berliner et al., "Novel Estrenes for Indusing Hypothalmic Effects", *Abstract No. 125:58846, WO 9610032*, 4 Apr. 1996 pp. 1–137.

Berliner et al., "Novel Androstanes for Inducing Hypothalamic Effects", *Abstracts No. 125:86979, WO 9610031*, 4 Apr. 1996, pp. 1–114.

Berliner et al., "Estrene Steroids as Neurochemical Initiators of Change in Human Hypothalamic Function and Related Pharmaceutical Compositions and Methods", *Abstract No. 122:152290, WO 9428903*, 22 Dec. 1994, pp. 1–94.

Berliner et al., "Androstane Steroids as Neurochemical Initiators of Change in Human Hypothalamic Function and Related Pharmaceutical Compositions and Methods", *Abstract No. 122:152289, WO 9428904*, 22 Dec. 1994, pp. 1–89.

Jin et al., "Stereospecific Synthesis of Trifluoromethylated 1,3,5-trienes", *Abstract No. 121:107573, Journal of Fluorine Chemistry*, 1994, 67:1–4.

Schweder et al., "DELTA. 16–20–keto Steroids by C–2 Elongation from DELTA.16–17 Substituted Steroids", *Abstract No. 120:31014, Journal Praktikal Chemistry*, 1993, 335(5), pp. 439–444.

Garcia-Velasco et al., *Aesth. Plast. Surg.* 19:451–454 (1995).

Axel, *Scientific American*, Oct. 1995 pp.154–159.

CA60:4412h, RN100930-51-6, Hsia et al, 1964.

*Primary Examiner*—Rebecca Cook
*Attorney, Agent, or Firm*—Fish & Richardson P.C.

[57] ABSTRACT

The invention relates to a method of altering hypothalamic function in an individual. The method comprises nasally administering a human vomeropherin, e.g. a 19-nor pregnane steroid, or a pharmaceutical composition containing a vomeropherin, such that the vomeropherin binds to a specific neuroepithelial receptor. The steroid or steroids is/are preferably administered in the form of a pharmaceutical composition containing one or more pharmaceutically acceptable carriers. Other embodiments of the invention include pharmaceutical compositions containing the steroids.

8 Claims, 16 Drawing Sheets

5,792,757

1

19-NOR-PREGNANE STEROIDS AS NEUROCHEMICAL INITIATORS OF CHANGE IN HUMAN HYPOTHALAMIC FUNCTION

CROSS REFERENCE TO RELATED APPLICATIONS

This application is a continuation-in-part of U.S. patent application Ser. No. 08/286,073, filed Aug. 4, 1994 now U.S. Pat. No. 5,563,131.

CROSS REFERENCE TO RELATED APPLICATIONS

This application is related to U.S. application Ser. No. 08/127,908, filed Sep. 28, 1993 which is a continuation-in-part of U.S. application Ser No. 07/903,604, filed 24 Jun., 1992, which in turn is a continuation-in-part of U.S. application Ser. No. 07/708,936, filed 31 May, 1991, which in turn is a continuation-in-part of U.S. application Ser. No. 07/638,185, filed 7 Jan., 1991, now abandoned.

The application also relates to U.S. application Ser. No. 08/127,980 filed Sep. 28, 1993 which is another continuation-in-part of U.S. patent application Ser. No. 07/903,604, U.S. patent application Ser. No. 08/077,359, filed 15 Jun., 1993, and to commonly assigned, co-pending U.S. patent application Ser. No. 07/903,525, filed 24 Jun., 1992 (a continuation-in-part of U.S. application Ser. No. 07/707,862, filed 31 May, 1991, which in turn is a continuation in-part of U.S. application Ser. No. 07/638,743, filed 7 Jan., 1991, now abandoned) entitled "Estrene Steroids as Neurochemical Initiators of Change in Human Hypothalamic Function and Related Pharmaceutical Compositions and Methods"; and to the commonly assigned, co-pending continuation-in-part of U.S. application Ser. No. 07/903,525, U.S. patent application Ser. No. 08/077,140. The aforementioned U.S. patent applications are each incorporated herein by reference.

Finally, this application may relate to U.S. patent application entitled "Fragrance Compositions Containing Human Pheromones, filed 24 Mar., 1992, U.S. application Ser. No. 07/856,435.

TECHNICAL FIELD

This invention relates generally to pharmaceutical compositions and methods for effectuating change in human hypothalamic function, thereby altering certain behavior and physiology mediated by the hypothalamus of individuals. More particularly, the invention relates to the use of 19-norpregnane steroids as neurochemical effectuators of physiology and behavior.

DESCRIPTION OF THE RELATED ART

The present invention relates to certain compounds, namely 19-norpregnane steroids, particularly 19-norpregnane steroids and related compounds as will be described herein, and methods of using these compounds as human vomeropherins in order to alter hypothalamic function, thereby affecting certain consequent behavior and physiology, e.g., the reduction of anxiety. The 19-norpregnane steroids are characterized by a four ring steroidal structure, methylation at the 13 position and ethylation at the 17-position. The 19-nor-pregnenes are a subset which have at least one double bond.

Ohloff, G. et al. (*Helv. Chim. Acta* (1983) 66:192–217), which is incorporated herein by reference, have shown that

2 several steroids (androstenes) have an odor which varies with different isomeric, diastereomeric, and enantiomeric forms. Some members of this group have been reported to act as a pheromone in some mammalian species for instance, 5α-androst-16-en-3-one and 5α-androst-16en-3α-ol in pigs (Melrose, D. R., et al., *Br. vet. J.* (1971) 127:497–502). These 16-androstenes produced by the boar induce mating behavior in estrus sows (Claus, et al., Experimentia (1979) 35:1674–1675).

In some studies it has been noted that, in some species, various characteristics of certain 16-androstenes (including 5α-Androst-16-en-3α-ol and 5α-Androst-16-en-3-one), such as concentration, metabolism, and localization, are sexually dimorphic (Brooksbank et al., J. Endocr. (1972) 52:239–251; Claus, et al., J. Endocr. (1976) 68:483–484; Rwan, et al., Med. Sci. Res. (1987) 15:1443–1444). For instance, 5α-Androst-16-en-3α-ol and 5α-Androst-16-en-3-one, as well as Androsta-4,16-dien-3-one, have been found at different concentrations in the peripheral blood, saliva and axillary secretions of men and of women (Kwan,T. X., et al., *Med. Sci. Res.* (1987) 15:1443–1444), and their function as a human pheromone, to the extent of affecting choice and judgement, has been suggested (Id.; see also Gower, et al., "The Significance of Odorous Steroids in Axillary Odour", In, *Perfumery*, pp. 68–72, Van Toller and Dodd, Eds., Chapman and Hall, 1988); Kirk-Smith, D. A., et al., *Res. Comm. Psychol. Psychiat. Behav.* (1978) 3:379). Androstenol (5α-androst-16-en-3α-ol) has been claimed to exhibit a pheromone-like activity in a commercial men's cologne and women's perfume (Andron for men and Andron for women by Jovan). Japanese Kokai No. 2295916, refers to perfume compositions containing androstenol and/or its analogues. 5α-Androstadien-3β-ol (and perhaps the 3α-ol) has also been identified in human axillary secretion (Gower, et al., Supra at 57–60. On the other hand, there is little agreement in the literature as to whether or not any putative pheromone actually plays any role in the sexual or reproductive behavior of mammals, particularly of humans. See: Beauchamp, G. X., et al., "The Pheromone Concept in Mammalian Chemical Communication: A Critique", In: *Mammalian Olfaction. Reproductive Processes and Behavior*, Doty R. L., Ed., Academic Press, 1976). See also: Gower, et al., supra at 68–73.

The pheromone properties of some estrene steroids for some mammalian species have been described. Michael, R. P. et al., *Nature* (1968) 218:746 refers to Estrogens (particularly Estradiol) as a pheromonal attractant of male rhesus monkeys.

Parrot, R. F., Hormones and Behavior (1976) 7:207–21S, reports Estradiol benzoate injection induces mating behavior in ovariectomized rats; and the role of the blood level of Estradiol in make sexual response (Phoenix, C. H., Physiol. and Behavior (1976) 16:305–310) and female sexual response (Phoenix, C. H., Hormones and Behavior (1977) 8:356–362) in Rhesus monkeys has been described. On the other hand, there is little agreement in the literature as to whether or not pheromones as such play any role in the reproductive behavior and interpersonal communication of mammals (Beuchamp, G. K., et al., "The Pheromone Concept in Mammalian Chemical Communication: A Critique", In: *Mammalian Olfaction Reproductive Processes. and Behavior*, Doty, R. L., Ed., Academic Press, 1976).

An embodiment of the subject invention concerns the non-systemic, nasal administration of certain 19-nor-pregnane and 19-nor-pregnene steroids to affect a specific behavioral or physiological response in human subjects, e.g., a reduction of negative affect, mood, and character traits. In particular, nasal administration provides for contacting neurochemical receptors of a heretofore poorly understood neuroendocrine structure, commonly known as the vomeronasal organ ("VNO"); also known as "Jacobson's organ"), with one or more steroid(s) or with compositions containing the steroid(s). This organ is accessed through the nostrils of most higher animals—from snakes to humans, and has been associated, inter alia, with pheromone reception in certain species (see generally Muller-Schwarze & Silverstein, *Chemical Signals*, Plenum Press, New York (1980)). The axons of the neuroepithelia of the vomeronasal organ, located supra palatinal, form the vomeronasal nerve and have direct synaptic connection to the accessory olfactory bulb and indirect input from there to the cortico-medial amygdaloid basal forebrain and hypothalamic nuclei of the brain. The distal axons of terminalis nerve neurons may also serve as neurochemical receptors in the VNO. Stensaas, L. J., et al., *J. Steroid Biochem. and Molec. Biol.* (1991) 39:553. This nerve has direct synaptic connection with the hypothalamus.

Johnson, A. et al. (J. Otolarynaoloav (1985) 14:71–79) report evidence for the presence of the vomeronasal organ in most adult humans, but conclude that the organ is probably non-functional. Contravening results which suggest that the VNO is a functional chemosensory receptor are reported by Stensaas, L., et al., suora; and by Moran, D. T., et al., Garcia-Velasco, J. and M. Mondragon; MontiBloch, L. and B. Grosser all in *J. Steroid Biochem. and Molec. Biol.* (1991) 39.

It is apparent that it would be desirable to identify and synthesize human vomeropherins and pheromones and to develop pharmaceutical compositions and methods of use to influence hypothalamic function. This invention relates to the unexpected discovery that, when nasally administered to human subjects, certain neurochemical ligands, particularly 19-nor-pregnane steroids, 19-nor-pregnene steroids and related compounds, or pharmaceutical compositions containing 19-nor-pregnanes, 19-nor-pregnenes or related compounds, specifically bind to chemoreceptors of certain nasal neuroepithelial cells and this binding generates a series of neurophysiological responses resulting in an alteration of hypothalamic function of an individual. When properly administered, the effect of certain of these compounds on the hypothalamus affects the function of the autonomic nervous system and a variety of behavioral-or physiological phenomena which include, but are not limited to the following: anxiety, premenstrual stress, fear, aggression, hunger, blood pressure, and other behavioral and physiological functions normally regulated by the hypothalamus. See Otto Appenzeller, *The Autonomic Nervous System. An Introduction of Basic and Clinical Concepts* (1990); Rorner, P. I. *Central nervous control of autonomic cardiovascular function*, and Levy N. M. and Martin, P. J. *Neural control of the heart*, both in *Handbook of Physiology: Section 2: Cardiovascular System—the heart*, Vol. I, Washington, D.C., 1979, American Physiological society; Fishman, A. P., et al. editors, *Handbook of Physiolofy: Section 3: Respiratory System. Vol. II. Control of Breathing*, Bethesda Md. 1986. American Physiological Society.

In some instances a single 19-nor-pregnane steroid, or related compound, is administered, in some instances combinations of 19-nor-pregnane steroids and/or related compounds are administered and in some instances one or more 19-nor-pregnane steroids are coadministered along with one or more estrane or estrene steroids, androstane or androstene steroids or a related compound.

BACKGROUND OF THE INVENTION

Definitions

An "affect" is a transient feeling state. Typical negative affects are feelings of nervousness, tenseness, shame, anxiousness, irritability, anger, rage, and the like. "Moods" are longer lasting feeling states such as guilt, sadness, hopelessness, worthlessness, remorsefulness, misery, unhappiness and the like. "Character traits" are more permanent aspects of an individual's personality. Typical negative character traits are sensitivity, regretfulness, blameworthiness, stubbornness, resentfulness, bitterness, timidness, laziness and the like.

"Pregnane steroids" are aliphatic polycyclic hydrocarbons characterized by a four-ring steroidal structure with a methylation at the 10- and 13-positions and ethylation (including unsaturated groups) at the 17-position. The 19-nor compounds lack a methyl or other carbon-containing substituent on C-10 where C-19 would normally be found. A pregnene is a subset of pregnanes commonly understood to mean that the compound has at least one double bond.

A "chemoreceptor" is a receptor molecule displayed on the surface of a "chemosensory" neuroepithelial cell which binds in a stereospecific fashion to a particular ligand or ligands. This specific binding initiates a signal transduction which initiates an afferent nerve impulse. Chemoreceptors are found, inter alia, in taste buds, olfactory epithelium and vomeronasal tissue.

"Pregnene steroids", as the term is used herein, are aliphatic polycyclic hydrocarbons with a four-ring steroidal structure, at least one double bond in the A-ring, methylation at the 10-position and 13-position, ethylation (including unsaturated groups) at the 17-position and an oxo, hydroxyl or hydroxyl derivative such as an alkoxy, ester, benzoate, cypionate, sulfate or glucuronide, at the 3-position. The 19-nor compounds lack a methyl or other carbon-container substituent or C-10 where C-19 would normally be found. Derivatives which contain these structural characteristics are also referred to generically as pregnene steroids.

The following structure shows the four-ring steroidal structure common to pregnane and pregnene steroids. In describing the location of groups and substituents, the following numbering system will be employed:

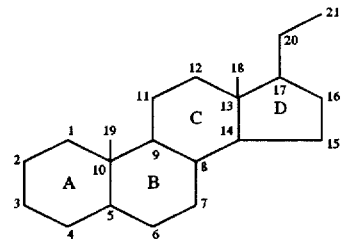

"Sexually dimorphic" refers to a difference in the effect of, or response to, a pharmaceutical agent between males and females of the same species.

An "effective amount" of a drug is a range of quantity and/or concentration which brings about a desired physiological and/or psychological effect when administered to an individual in need of the drug. In the present case, a needy individual is one with a physiological or behavioral trait which is normally regulated by the hypothalamus and wherein it is desirable to affect the function of the hypothalamus or the trait. The effective amount of a given drug may vary depending upon the function to be affected, the desired effect, route of administration, and the like. For example, when the steroid in administered as a solution applied to the facial skin of a subject an effective concentration is from 1 microgram/ml to 100 µg/ml, preferably 10 to 50 µg/ml and most preferably 20 to 30 µg/ml. When the steroid is introduced directly into the VNo an effective amount is about 1 picogram to about 1 nanogram, more preferably about 10 picograms to about 50 picograms. When the steroid is administered to the nasal passage, by ointment, cream or aerosol, or the like, an effective amount is about 100 pg to about 100 micrograms, preferably about 1 ng to about 10 micrograms. It follows that some drugs may be effective when administered by some routes, but not effective when administered by other routes.

The "hypothalamus" is the portion of the diencephalon comprising the ventral wall of the third ventricle below the hypothalamic sulcus and including structures forming the ventricle floor, including the optic chiasma, tuber cinereum, infundibulum, and mammallary bodies. The hypothalamus regulates the autonomic nervous system and controls several physiological and behavioral functions such as the so-called fight and flight responses, sexual motivation, water balance, sugar and fat metabolism, hunger, regulation of body temperature, endocrine secretions, and others. The hypothalamus is also the source of vasopressin which regulates blood pressure, and oxytocin which induces parturition and milk release. All hypothalamic functions are potentially modulatable by the vomeropherin therapy described herein.

A "ligand", as used herein, is a molecule which acts as a chemical signal by specifically binding to a receptor molecule displayed on the surface of a receptor cell, thereby initiating a signal transduction across the cell surface. Binding of ligands to chemosensory receptors can be measured. Chemosensory tissue, such as vomeronasal neuroepithelium or olfactory neuroepithelium, contains a multiplicity of neuroreceptors cells, each displaying at least one cell surface receptor. Many of the receptor molecules have identical ligand specificity. Therefore, when the tissue is exposed to a ligand for which it has specificity (for example a exposure of the VNO to a vomeropherin) a summated change in cell surface receptor potential can be measured.

As used herein, "lower alkyl" means a branched or unbranched saturated hydrocarbon chain of 1 to 4 carbons, such as, for example, methyl, ethyl, n-propyl, i-butyl and the like. "Alkoxy" as used herein is used in its conventional sense to mean the group —OR wherein R is alkyl as herein defined.

A "pheromone" is a substance that provides chemical means of communication between members of the same species through secretion and peripheral chemoreception. In mammals pheromones are usually detected by receptors in the vomeronasal organ of the nose. Commonly, pheromones effect development, reproduction and related behaviors. A "vomeropherin" is a more general term which includes pheromones and describes a substance from any source which functions as a chemosensory messenger, binds to a specific vomeronasal neuroepithelial receptor, and induces a physiological or behavioral effect. The physiologic effect of a "vomeropherin" is mediated through the vomeronasal organ.

A picogram (pg) is equal to 0.001 nanograms (ng). A ng is equal to 0.001 micrograms (µg). A µg is equal to 0.001 mg.

The invention is directed to a group of certain 19-nor pregnane steroids.

A subset of 19-norpregnanes within the group are believed to be novel. Syntheses are described herein for the following compounds as designated on the chart: Chart 1 includes 19-norpregnanes to which the invention is directed, but do not limit its scope. The synthesis diagrams that follow depict intermediate and substructure syntheses for the preparation of these 19-norpregnanes.

SUMMARY OF THE INVENTION

Figure 1:
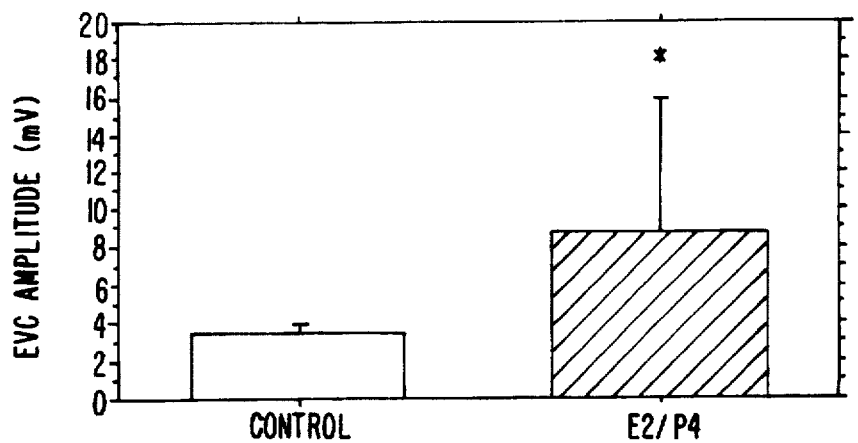
FIG. 1 and FIG. 2 show the EVG and vomeronasal nerve discharge frequency, respectively, of steroid E2/P4 and control, in female rats.

Accordingly, it is an object of this invention to provide pharmaceutical compositions which contain human vomeropherins or pheromones and are suitable for nasal administration in an individual.

It is also an object of this invention to provide methods of using these compositions to alter hypothalamic function of an individual.

It is a further object of this invention to provide methods of using these compositions to affect physiological and behavioral functions of individuals which are normally regulated by the hypothalamus.

Finally, it is an object of this invention to provide methods of altering hypothalamic function which have the following advantages: 1) administration directly to the chemoreceptors in the nasal passage and the vomeronasal organ, without pills or needles—i.e., non-invasively; 2) a mode of drug action through the nervous system and not through the circulatory system—thus brain function can be affected without consideration of the bloodbrain barrier; 3) a direct means of affecting the hypothalamus—there is only one synaptic junction between pheromone receptors and the hypothalamus; and, 4) providing a highly specific drug effect, thereby greatly reducing the potential for undesirable side-effects—this because sensory nerves are addressed to a specific location in the brain. Additional objects, advantages and novel features of the invention will be set forth in part in the description which follows, and in part will become apparent to those skilled in the art upon examination of the following, or may be learned by practice of the invention.

Objects of this invention are achieved by providing a pharmaceutical composition suitable for nasal administration in an individual. The composition contains a pharmaceutically acceptable carrier and a pregnane steroid with the formula:

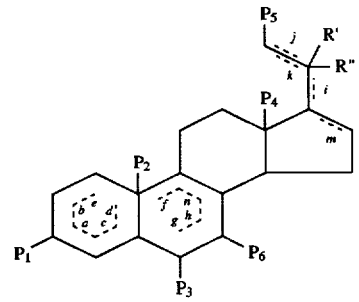

wherein $P_1$ is oxo, α- or β-hydroxy, α- or β-acetoxy, α- or β-propionoxy, α- or β-lower acetoxy, α- or β-lower acyloxy, or α- or β-benzyloxy;

"a", "b", "c", "d", "e", "f", "g", "h", "i", "j", "m" and "n" are alternative sites for optional double bonds, and "k" may be absent or present with "j" to form a triple bond;

$P_2$ is hydroxy, hydrogen, lower alkoxy of 1 to 6 carbon atoms, or $P_2$ is absent;

$P_3$ is oxo, hydrogen, hydroxy, lower alkoxy of 1–6 carbon atoms or halo;

$P_4$ is methyl or ethyl;

$P_5$ is hydrogen, methyl or halo;

$P_6$ is hydrogen or methyl.

One class of preferred steroid compositions contain steroids wherein "d" is a double bond, and optionally "b" is present as a double bond. Another preferred class has "a", "d" and "e" present, and g or h are optionally present. If "g" is present in this case, then "n" is optionally present. Another preferred class has "c" present, with "f" optionally present.

The novel class of 19-nor-pregnanes are those of the above formula, excluding the following compounds in the instances where $P_3$ and $P_6$ are hydrogen; "f", "n", "h" and "g" are absent; $P_4$ is methyl and R' and R" are not halo:

i) when $P_1$ is oxo, "c" is present and $P_2$ and $P_5$ are hydrogen; then either of "j" or "i" cannot be present alone, "m" and "j" cannot be present together, or "i" and "j" cannot be present together, or "m", "j" and "k" cannot be present together, and at least one of "i", "j" and "k" must be present;

ii) when $P_1$ is OH, "a", "d" and "e" are present and $P_5$ is hydrogen, then any of "j", "i", or "m" cannot be present alone, or "j" and "k" cannot be present together, or "i" and "j" cannot be present together, or "m", "j" and "k" cannot be present together, and at least one of "i", "j", "k" and "m" must be present;

iii) when $P_1$ is beta-OH, "c" is present, and $P_2$ and $P_5$ are hydrogen, then "i" and "j" cannot be present together, or "m", "j" and "k" cannot be present together;

iv) when $P_1$ is —OME and "d" and "b" are present, then either of "j" and "i" cannot be present alone;

v) when $P_1$ is oxo and "d" is present and $P_5$ is hydrogen; then "i" cannot be present alone or "j" and "k" cannot be present together.

The term lower alkyl, lower alkoxy, etc., is meant to encompass carbon chains of 1 to 6 carbon atoms, preferably 1 to 4 carbon atoms.

Other objects of this invention are achieved by providing a method of altering hypothalamic function and/or autonomic function in an individual. A ligand for a chemoreceptor displayed on the surface of a nasal neuroepithelial cell is provided wherein the cell is a part of tissue other than olfactory epithelia; and, the ligand is administered within a nasal passage of the individual such that the ligand binds specifically to the chemoreceptor, resulting in an alteration of hypothalamic function of the individual.

All embodiments of this application relate to and include the functional equivalents of the steroid structures disclosed in these embodiments and to those modified steroids which demonstrate said functional equivalence.

In the following chart, particularly preferred 19-nor-pregnanes are shown.

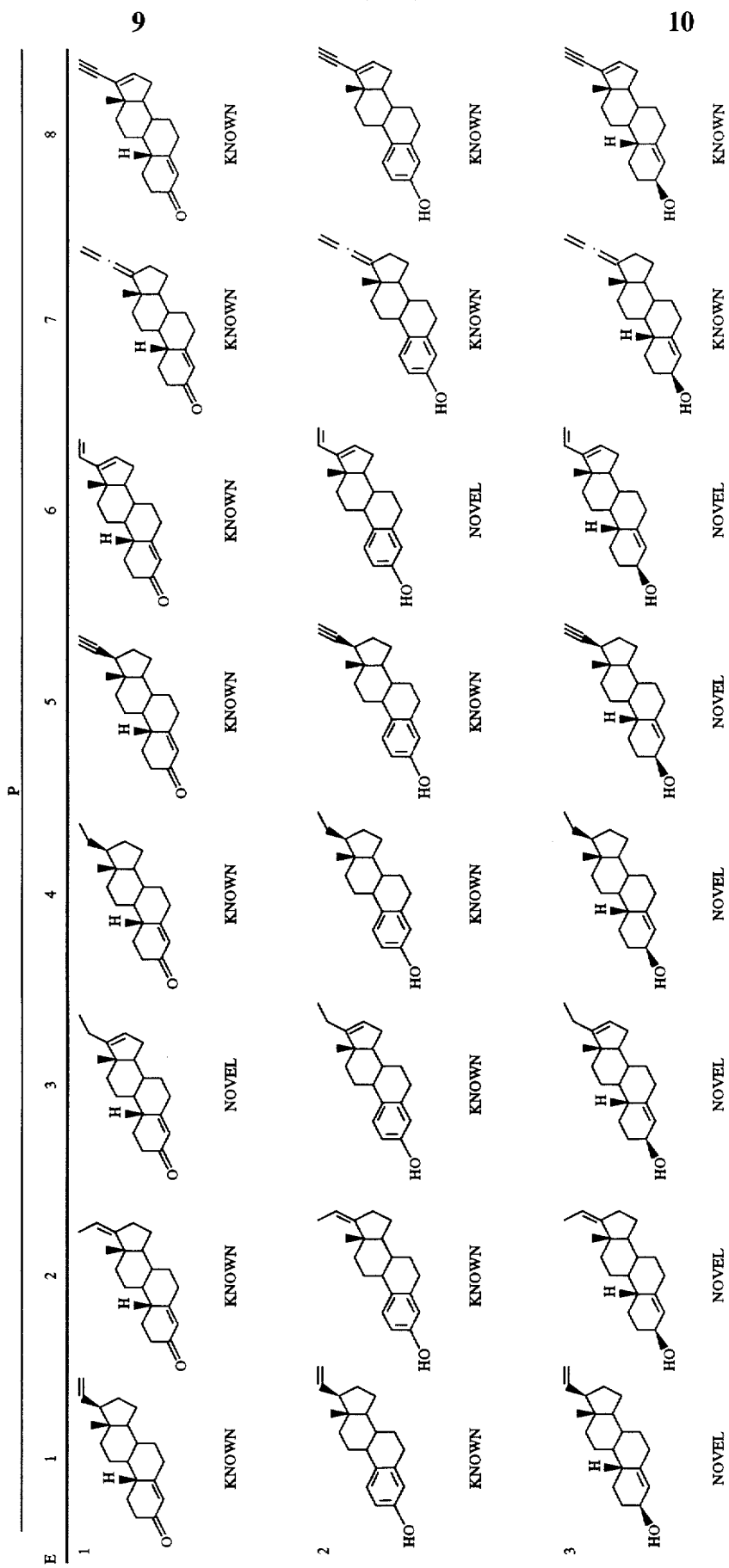

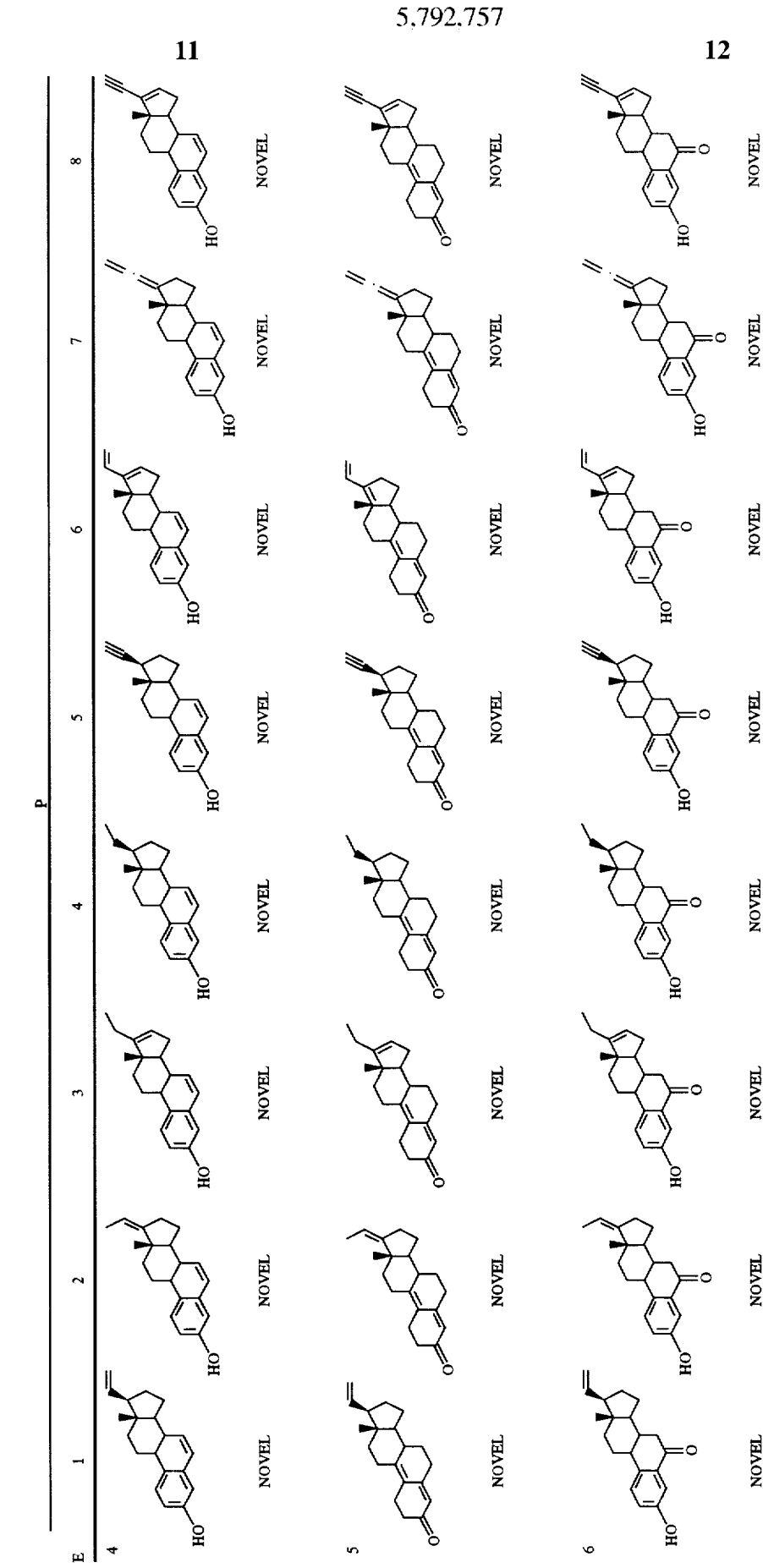

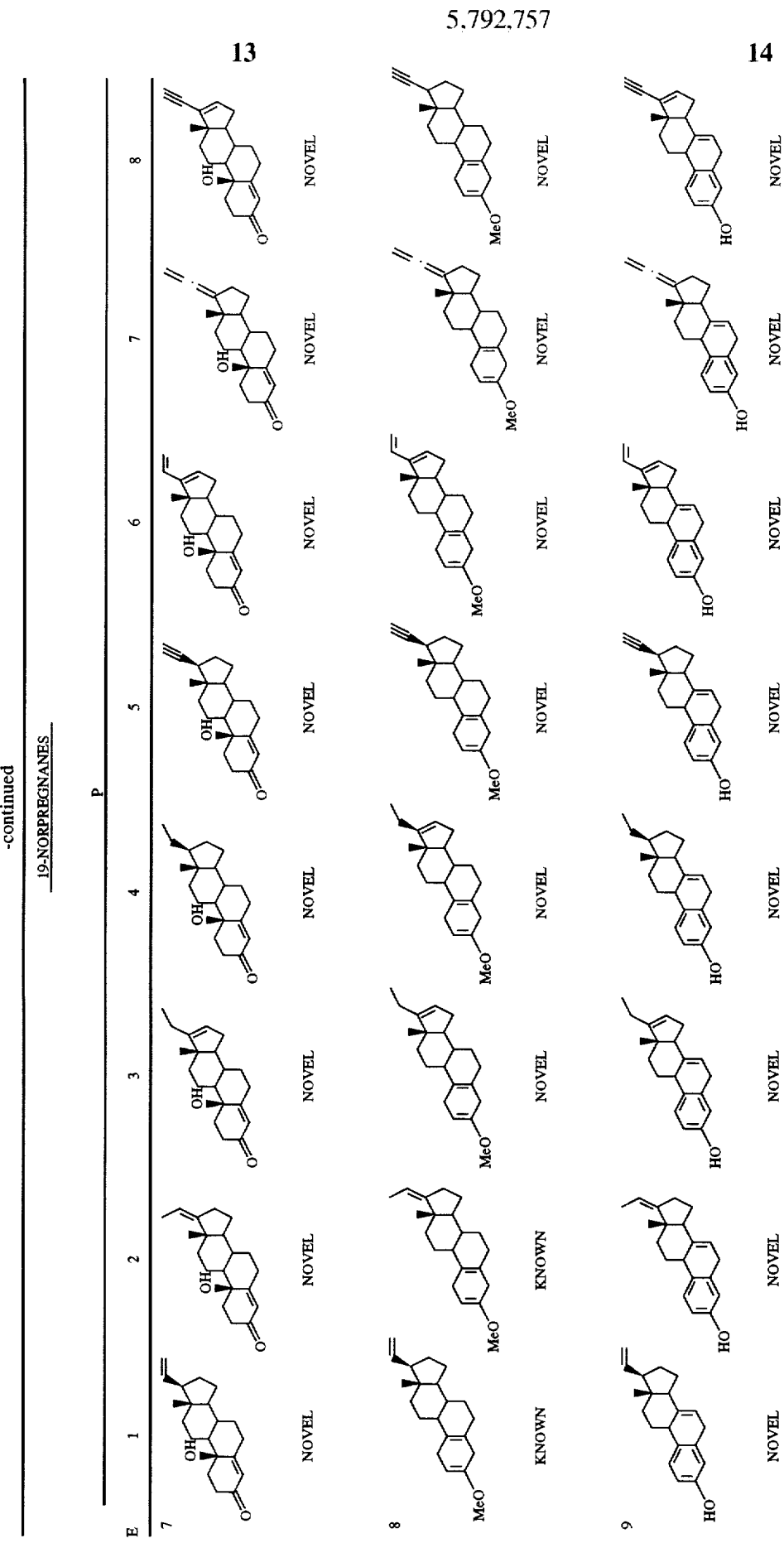

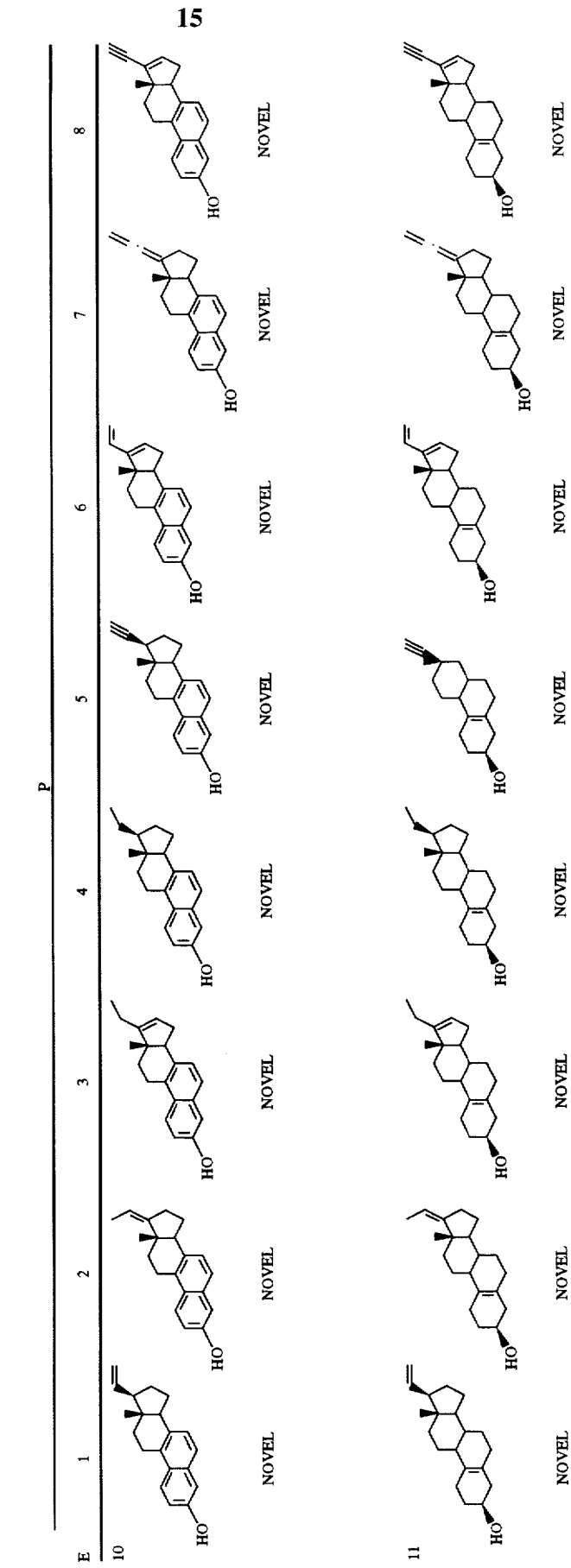

-continued

19-NORPREGNANES

| E | 1 | 2 | 3 | 4 | P 5 | 6 | 7 | 8 |
|---|---|---|---|---|---|---|---|---|
| 12 | NOVEL | NOVEL | NOVEL | NOVEL | NOVEL | NOVEL | NOVEL | NOVEL |
| 13 | NOVEL | KNOWN | NOVEL | NOVEL | KNOWN | NOVEL | NOVEL | NOVEL |

SUBSTRUCTURE SYNTHESIS: TYPE E

E1:

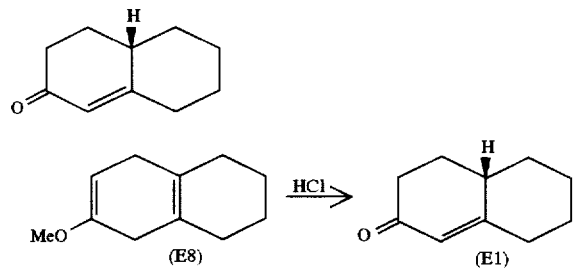

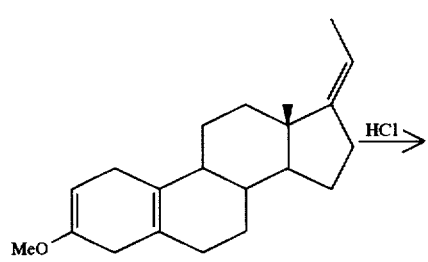

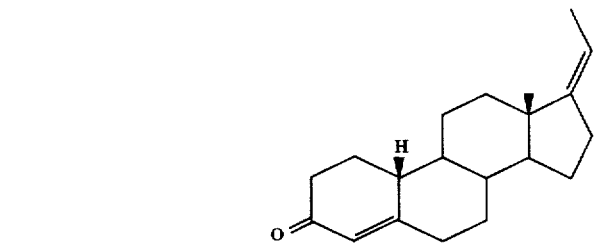

Frank B. Colton, Leonard N. Nysted, Byron Riegel, and Albert L. Raymond, J. Amer. Chem. Soc., 1957, 79, 1123.

Also a commercially available substructure, for example 17 α-ETHYNYL-19-NORTESTOSTERONE.

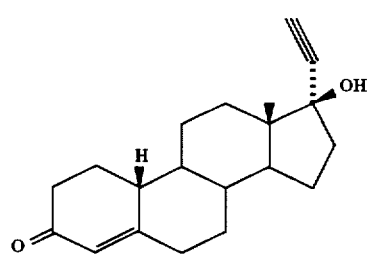

E2:

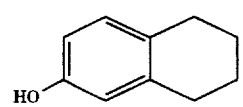

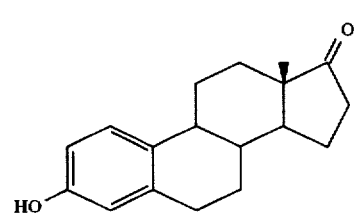

-continued
SUBSTRUCTURE SYNTHESIS: TYPE E

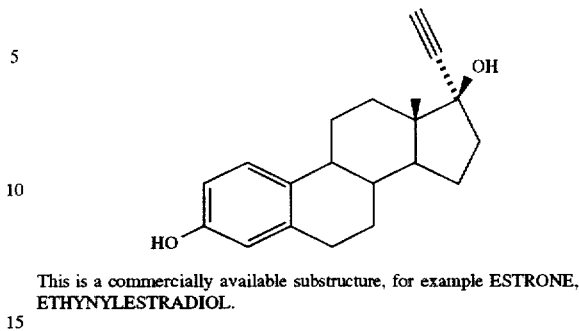

This is a commercially available substructure, for example ESTRONE, ETHYNYLESTRADIOL.

E3:

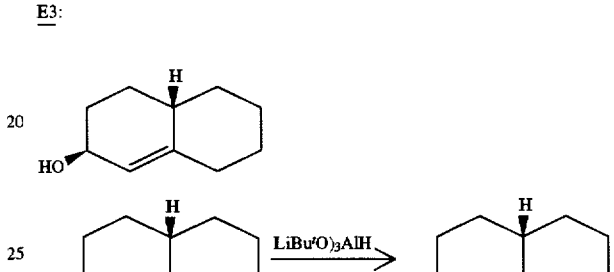

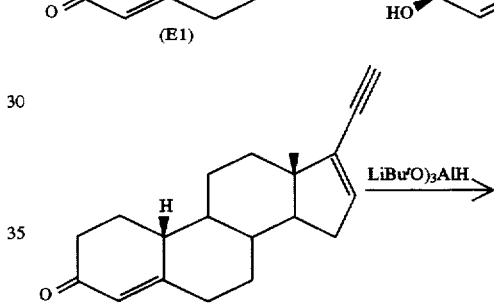

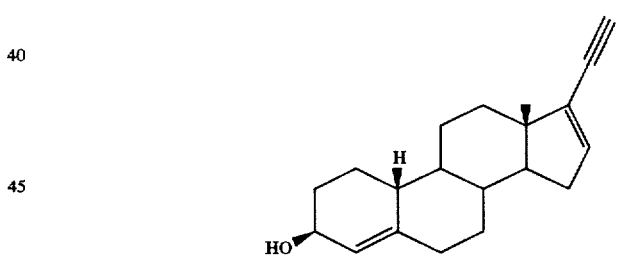

Pierre Crabble, U.S. Pat. No. 3,492,318, 1970.

E4:

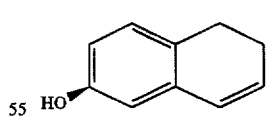

This is a commercially available substructrue, for example 6-DEHYDROESTRONE.

E5:

SUBSTRUCTURE SYNTHESIS: TYPE E
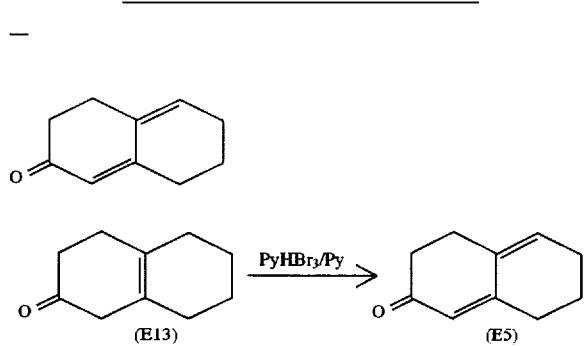
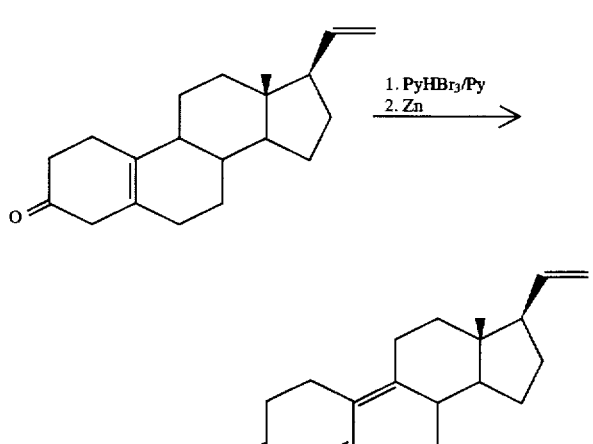
See Example.
E6:
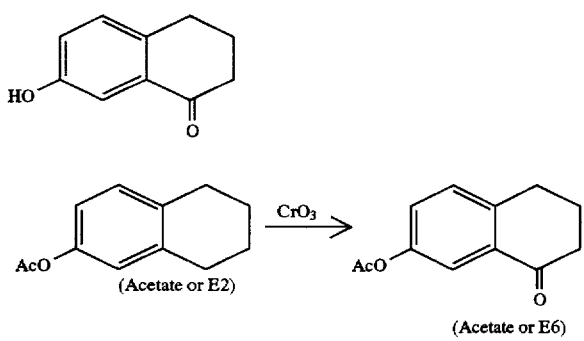
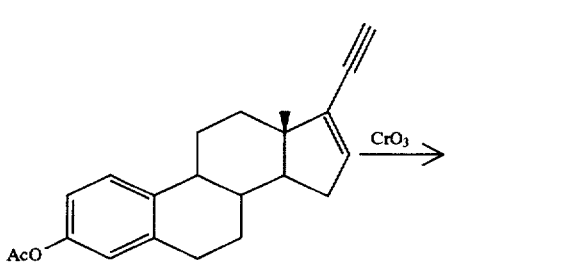
SUBSTRUCTURE SYNTHESIS: TYPE E
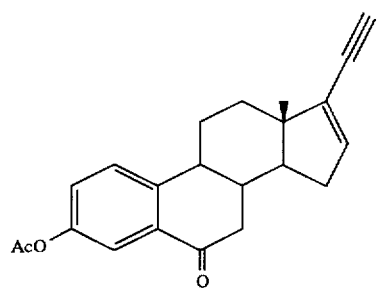
See Example.
E7:
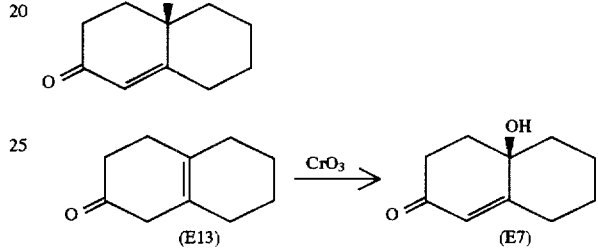
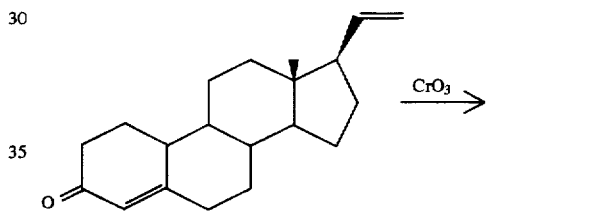
See Example.
E8:
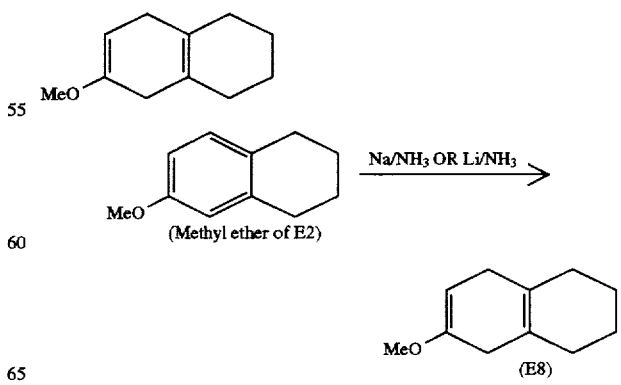

-continued
SUBSTRUCTURE SYNTHESIS: TYPE E

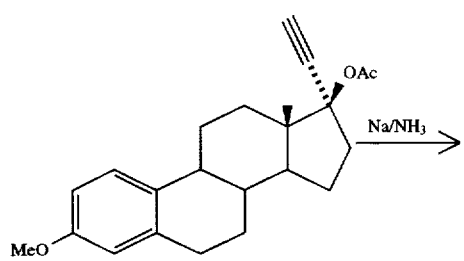

O. I. Fedorova, O. S. Anisimova, and G. S. Grinenko, Khim. Prir. Soedin., 1976, 2, 180.

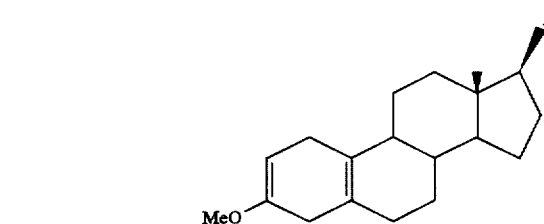

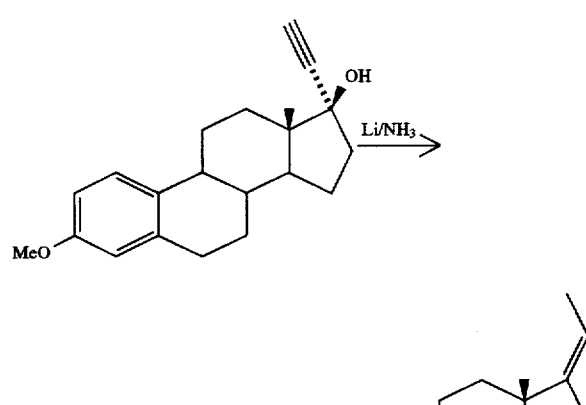

Frank B. Colton, Leonard N. Nysted, Byron Riegel, and Albert L. Raymond, J. Amer. Chem. Soc., 1957, 79, 1123.

E9:

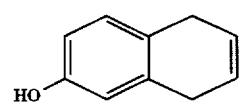

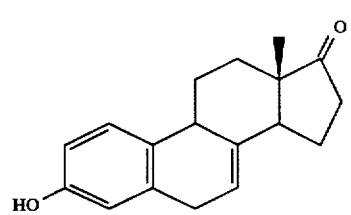

This is a commercially available substructrue, for example EQUILIN.

-continued
SUBSTRUCTURE SYNTHESIS: TYPE E

E10:

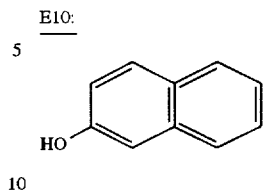

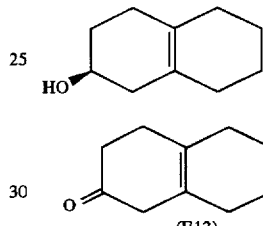

This a commercially available substructure, for example EQUILENIN.

E11:

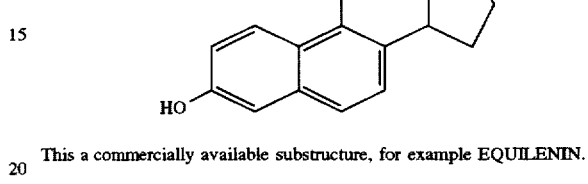

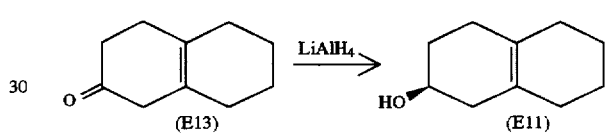

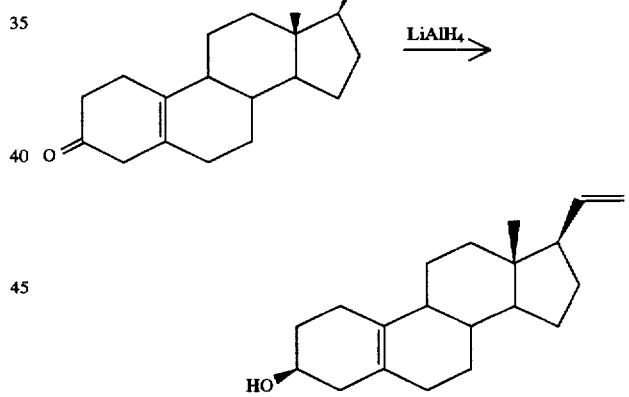

See Example.

E12:

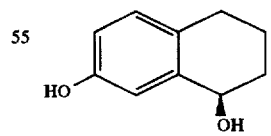

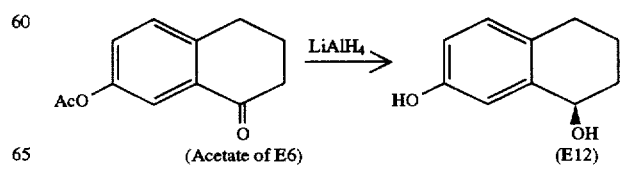

-continued
SUBSTRUCTURE SYNTHESIS: TYPE E
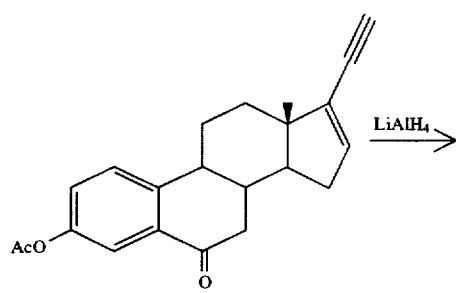
See Example.
E13:
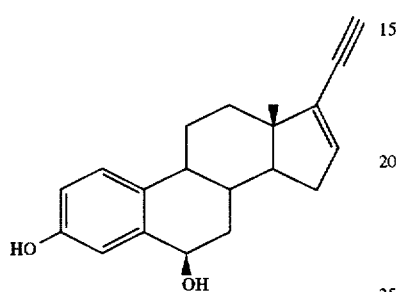
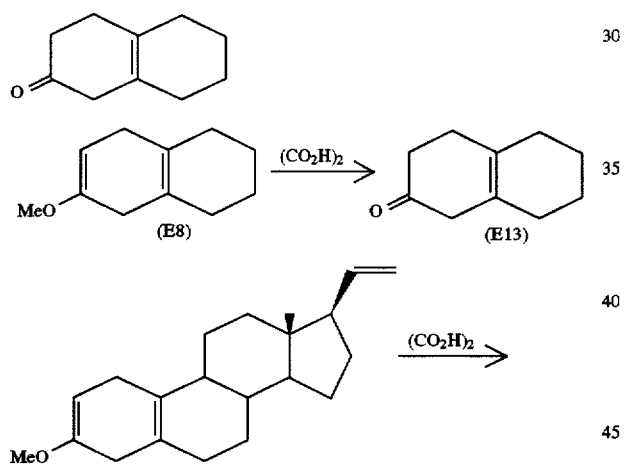
See Example.
SUBSTRUCTURE SYNTHESIS: TYPE P
P1:
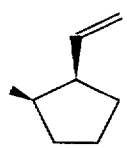
-continued
SUBSTRUCTURE SYNTHESIS: TYPE P
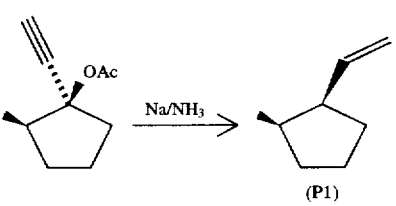
(P1)
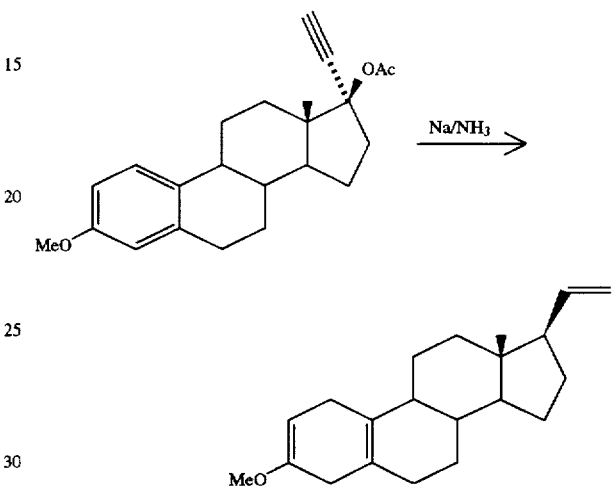
O. I. Fedorova, O. S. Anisimova, and G. S. Grinenko, Khim. Prir. Soedin., 1976, 2, 180.
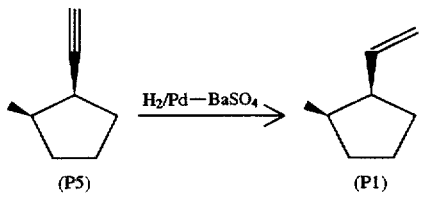
(P5)                (P1)
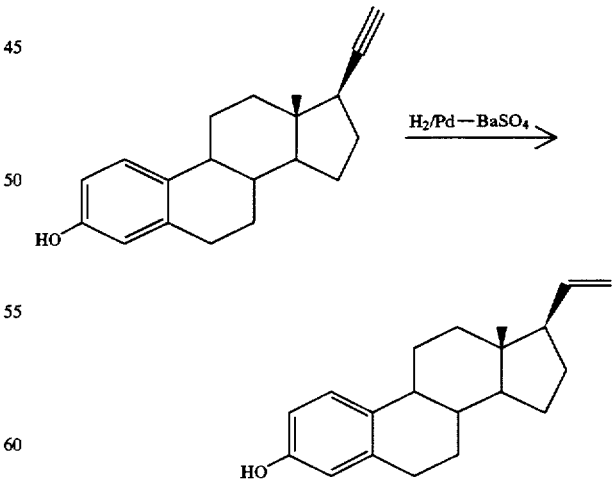
Richard H. Peters, David F. Crowe, Mitchell A. Avery, Wesley K. M. Chong, and Masato Tanabe, J. Med. Chem., 1989, 32, 1642.
Also See Example.

-continued
SUBSTRUCTURE SYNTHESIS: TYPE P
P2:
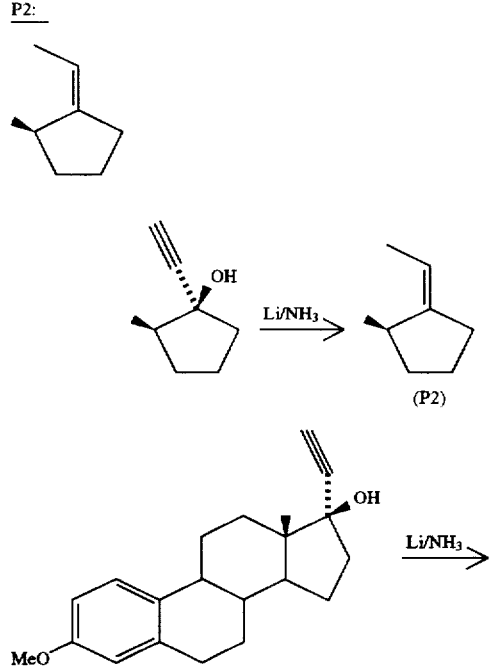
Frank B. Colton, Leonard N. Nysted, Byron Riegel, and Albert L. Raymond, J. Amer. Chem. Soc., 1957, 79 1123.
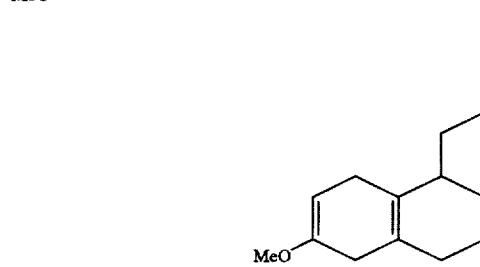
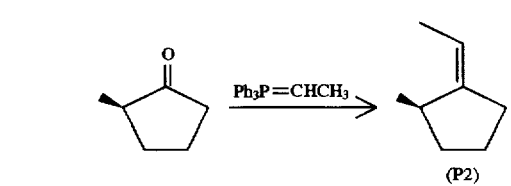
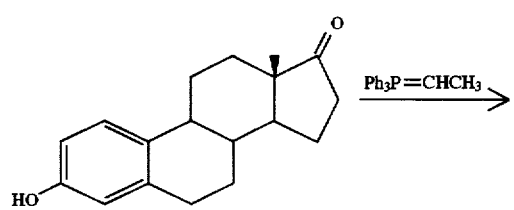
-continued
SUBSTRUCTURE SYNTHESIS: TYPE P
Richards H. Peters, David F. Crowe, Mitchell A. Avery, Wesley K. M. Chong, and Masato Tanabe, J. Med. Chem., 1989, 32, 1642.
P3:
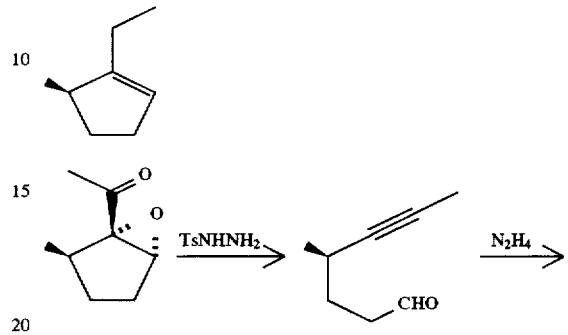
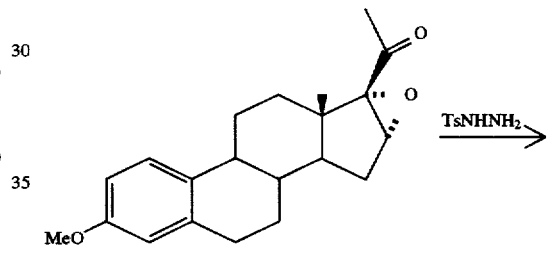
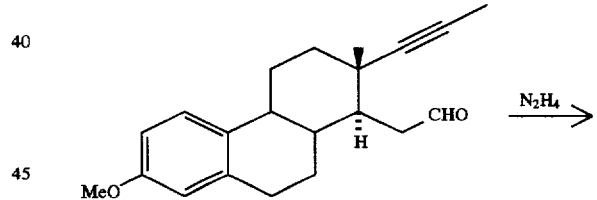
H. Kaufmann, P. Wieland, and J. Kalvoda, Helv. Chim. Acta., 1972, 55(2), 381.
P4:
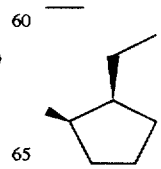

29
-continued
SUBSTRUCTURE SYNTHESIS: TYPE P
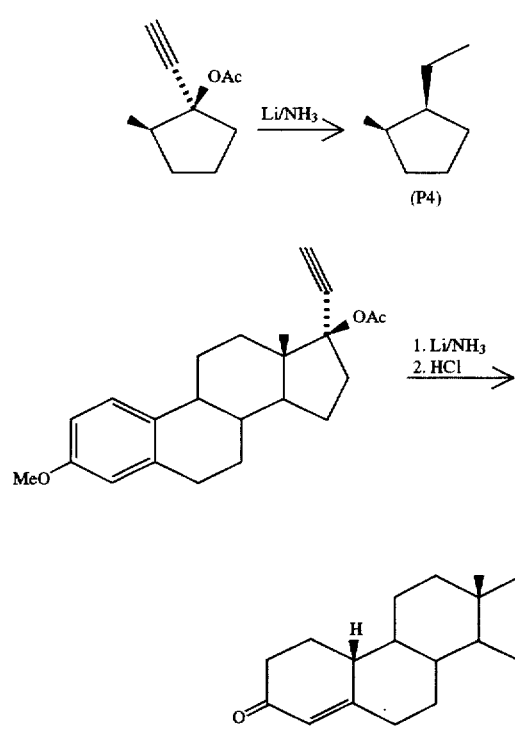
O. I. Fedorova, O. S. Anisimova, and G. S. Grinenko, Khim. Prir. Soedin., 1976, 2, 180.
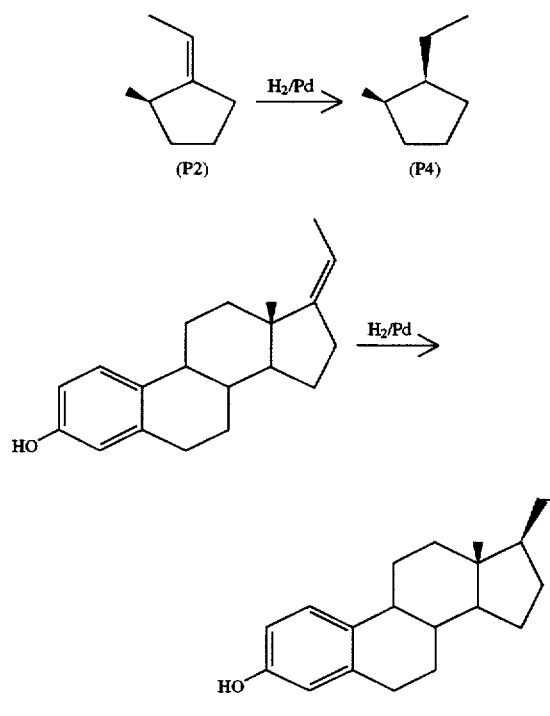
Richard H. Peters, David F. Crowe, Mitchell A. Avery, Wesley K. M. Chong, and Masato Tanabe, J. Med. Chem., 1989, 32, 1642.
30
-continued
SUBSTRUCTURE SYNTHESIS: TYPE P
P5:
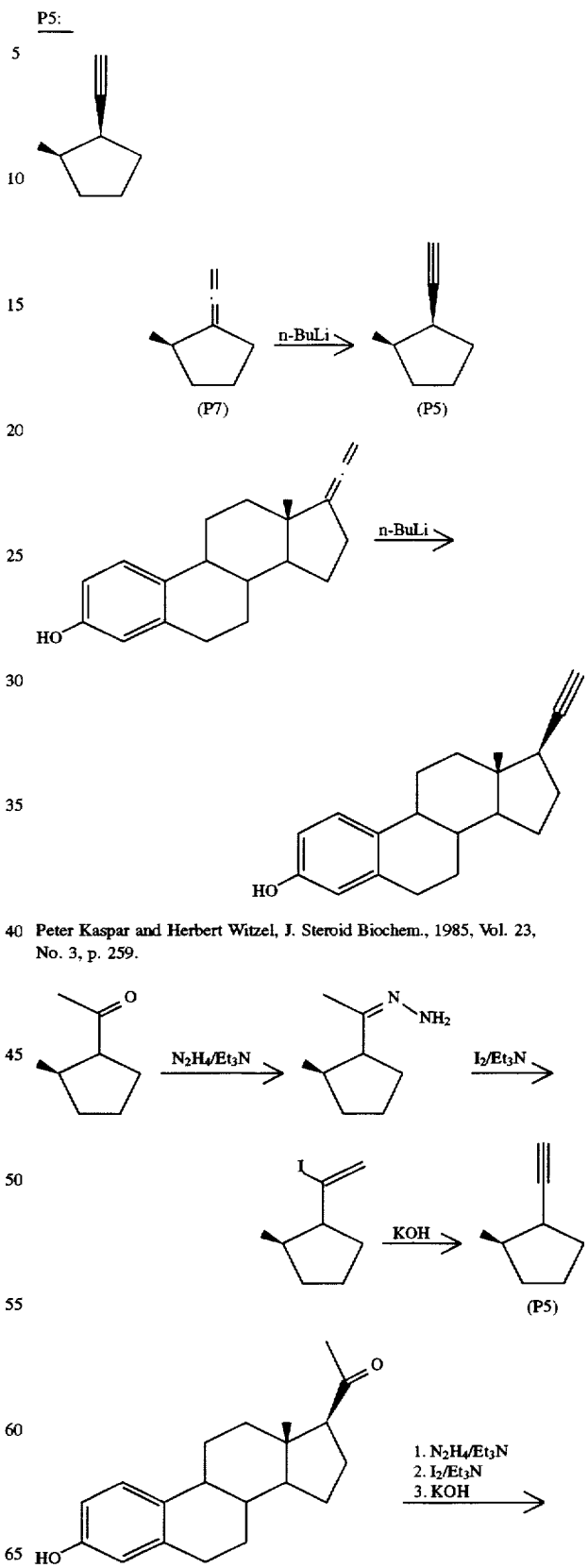
Peter Kaspar and Herbert Witzel, J. Steroid Biochem., 1985, Vol. 23, No. 3, p. 259.

31
-continued
SUBSTRUCTURE SYNTHESIS: TYPE P
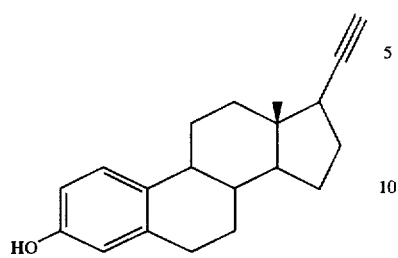
Richard H. Peters, David R. Crowe, Mitchell A. Avery, Wesley K. M. Chong, and Masato Tanabe, J. Med. Chem., 1989, 32, 1642.
P6:
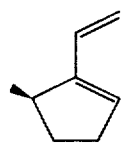
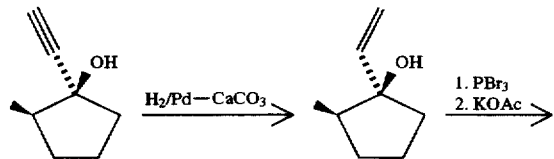
(P6)
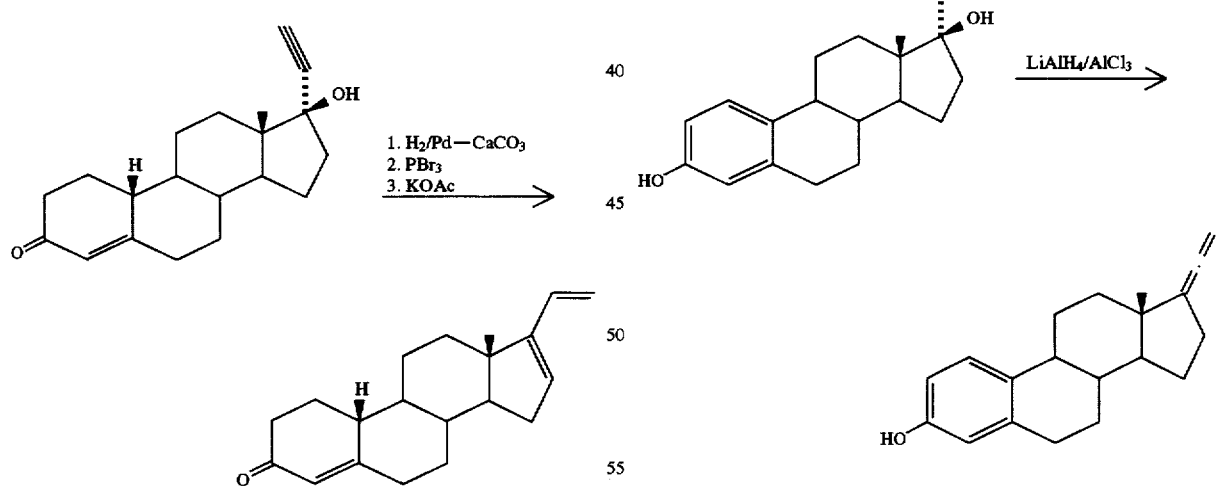
Frank B. Colton, U.S. Pat. No. 2,840,582, 1958.
P7:
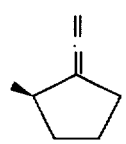
32
-continued
SUBSTRUCTURE SYNTHESIS: TYPE P
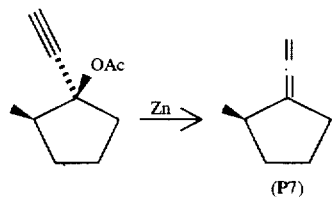
(P7)
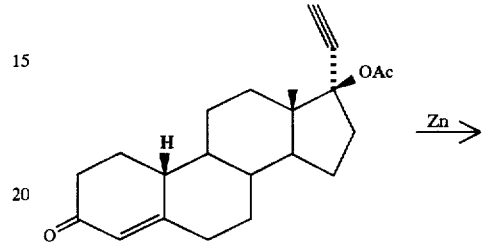
Pierre Crabble and Esperanza Velarde, U.S. Pat. No. 3,681,410, 1972.
Peter Kaspar and Herbert Witzel, J. Steroid. Biochem., 1985, Vol. 23, No. 3, P. 259.
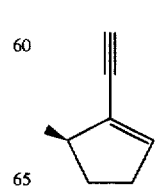

33
-continued
SUBSTRUCTURE SYNTHESIS: TYPE P

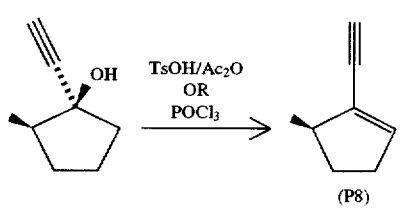

(P8)

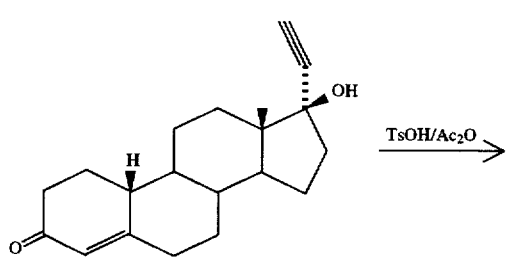

Pierre Crabble, U.S. Pat. No. 3,492,318, 1970.

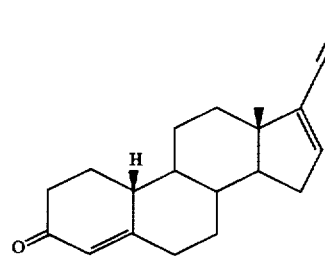

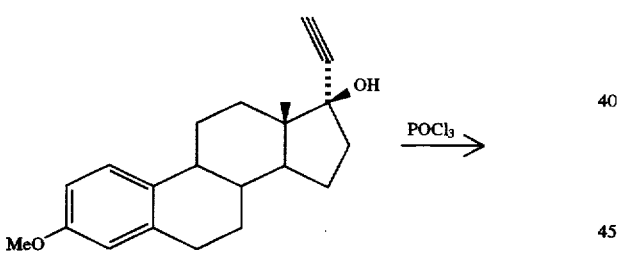

Klaus Prezewowsky and Rudolf Wiechert, U.S. Pat. No. 3,682,983, 1972.

METHYL NORPREGNANES

19-Norpregnanes in this series may be prepared with a methyl group in the 6α, 7α, 18, 20, or 21 positions.

U.S. Pat. No. 3,681,410 teaches preparation of 6α-methyl analogs.

34
-continued
METHYL NORPREGNANES

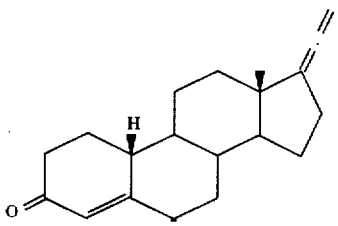

U.S. Pat. No. 3,682,983 teaches preparation of 18-methyl analogs.

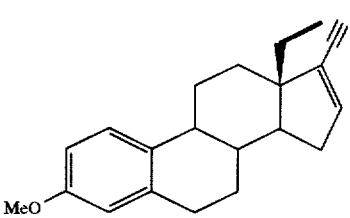

U.S. Pat. No. 3,492,318 teaches preparation of 7α, 18, and 21-methyl analogs.

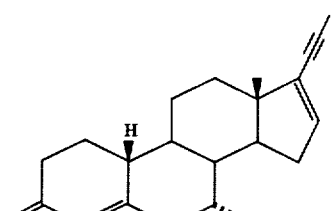

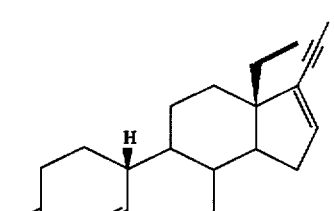

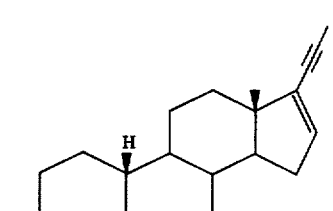

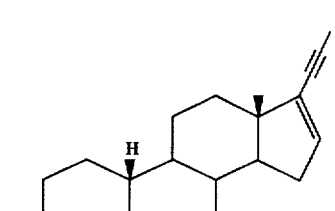

21-methyl analog:

35
-continued
METHYL NORPREGNANES
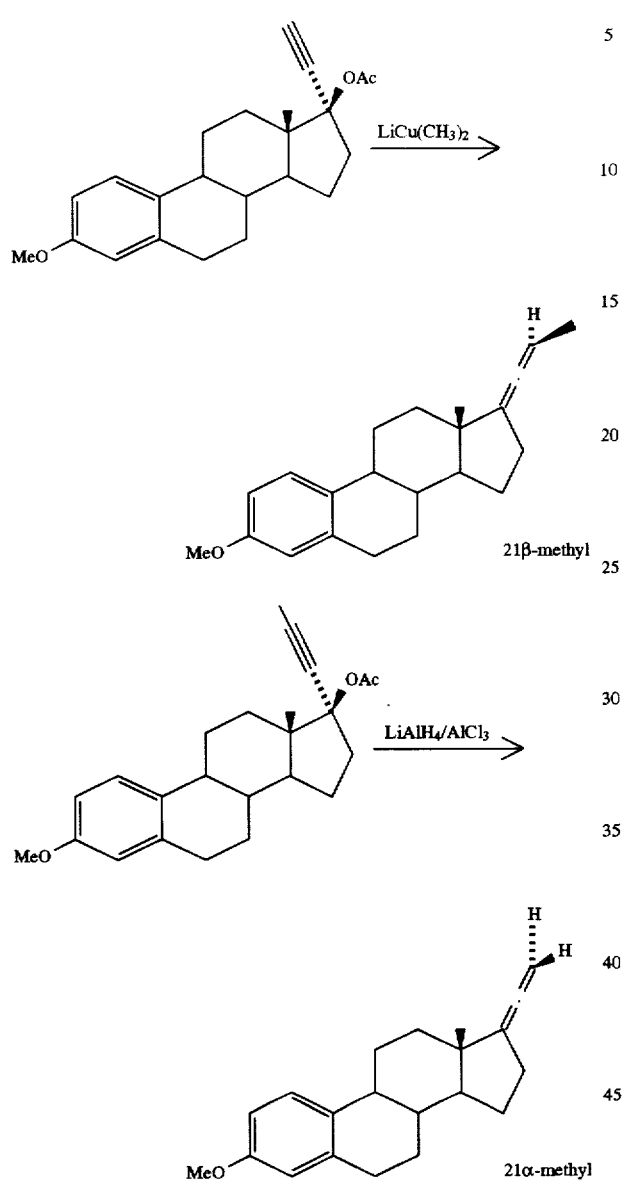
L.A. Van Dijck, B.J. Lankwerden, J.G.C.M. Vermeer, and A.J.M. Weber Recl. Tray. Chim, Pays-Bas Belg., 1971, 90, 801.
7α, 18, 20, and 21-methyl analogs.
36
-continued
METHYL NORPREGNANES
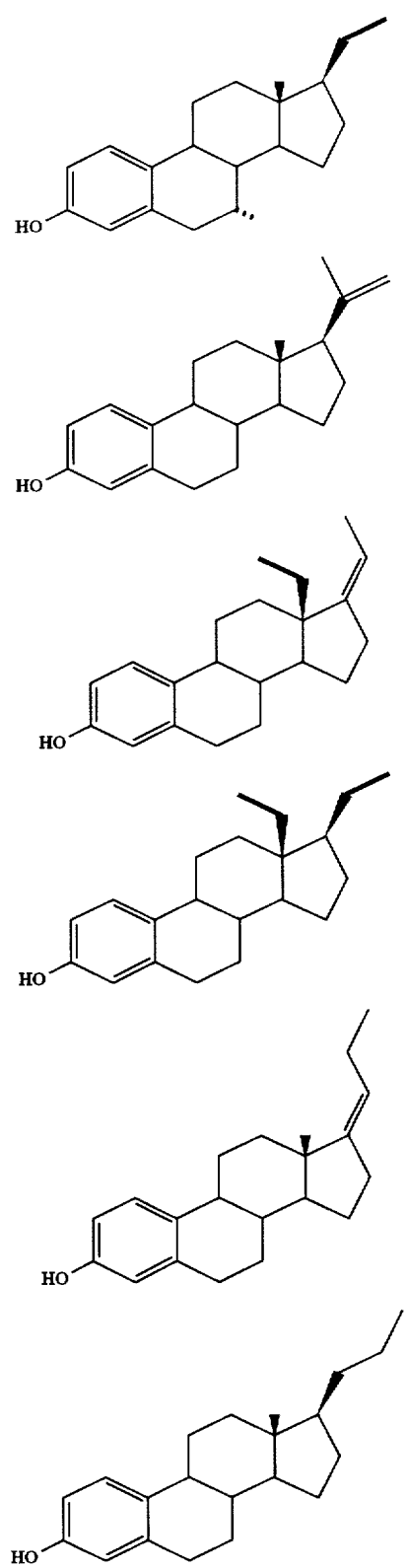
Richard H. Peters, David F. Crowe, Mitchell A. Averey, Wesley K.M. Chong, and Masato Tanabe, J. Med. Chem., 1989, 32, 1642.

-continued
METHYL NORPREGNANES

In addition certain methylated precursors are commercially available, for example:

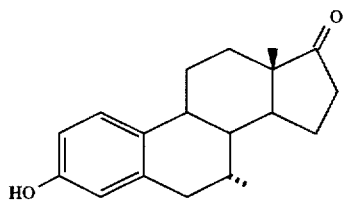

7α-METHYLESTRONE

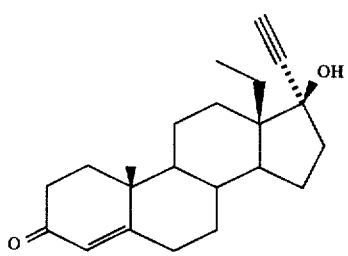

NORGESTREL

From these, 7α-methyl or 18- methyl analogs may be made of substances wherein estrone or 17α-ethynyl-19-nortestosterone (norethindrone) are the precursors, respectively.

HALONORPREGNANES

U.S. Pat. No. 2,840,582 teaches the preparation of:

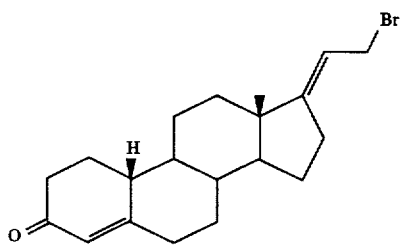

U.S. Pat. No. 3,681,410 teaches the preparation of:

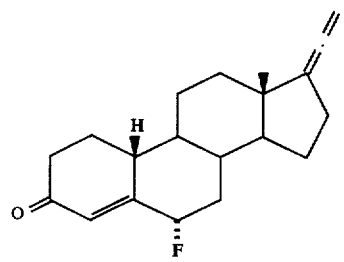

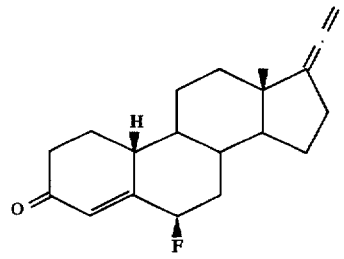

-continued
HALONORPREGNANES

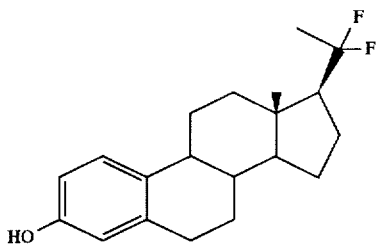

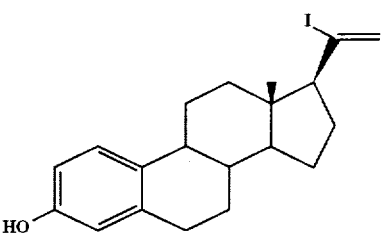

Richard H. Peters, David F. Crowe, Mitchell A. Avery, Wesley K.M. Chong, and Masato Tanabe, J. Med. Chem., 1989, 32, 1642.

Alkoxy derivatives are prepared from their corresponding hydroxy steroids by reaction with an alkylating agent such as trimethyloxonium fluoroborate, triethyloxonium fluoroborate or methylfluorosulfonate in an inert chlorocarbon solvent such as methylene chloride. Alternatively, alkylating agents such as alkyl halides, alkyl tosylates, alkyl mesylates and dialkylsulfate may be used with a base such as NaH, KM or KOBut, silver oxide or barium oxide in polar, aprotic solvents as for example, DMF, DMSO and hexamethylphosphoramide.

General procedures for synthetic reactions of steroids are known to those skilled in art. Where time and temperature of reactions must be determined, these can be determined by a routine methodology. After addition of the required reagents, the mixture is stirred under an inert atmosphere and aliquots are removed at hourly intervals. The aliquots are analyzed by chromatography to monitor the disappearance of starting material, at which point the work-up procedure is initiated. If the starting material is not consumed within twenty-four hours, the mixture is heated to reflux and hourly aliquots are analyzed, as before, until the starting material disappears. In this case the mixture is allowed to cool before the work-up procedure is initiated.

Purification of the products is accomplished by means of chromatography and/or crystallization, as known to those skilled in the art.

Pharmaceutical Compositions and Methods of Use

An embodiment of the subject invention is a method of altering the hypothalamic function of an individual. Another embodiment is altering an autonomic function of an individual. These autonomic functions include but are not limited to heart rate, respiratory rate, brain wave patterns (percentage alpha cortical activity), body temperature. Other embodiments include, but are not limited to, methods of diminishing negative affect, negative mood or neqative character traits of an individual. Another embodiment is a method of treating female premenstrual stress. All of these embodiments are accomplished by means of the non-systemic, nasal administration of certain pregnane steroids, combinations of pregnane steroids and combinations of one or more pregnane steroids and one or more androstane and/or estrene steroids.

This particular mode of administration is distinguished from alternative modes, such as ingestion or injection, in several important ways, these by virtue of the direct contact with the VNO provided by the nasal administration of the steroid ligand. In the methods of this invention, the appropriate ligand is administered directly to the chemoreceptors in the nasal passage and the vomeronasal organ, without pills or needles—i.e., non-invasively. Drug action is mediated through binding of the ligands, described herein, to specific receptors displayed by neuroepithelial cells in the nose, preferably in the VNO. This furthermore, the mode of drug action is through the nervous system and not through the circulatory system—thus brain function can be affected without consideration of the blood-brain barrier. These methods of treatment provide a direct means of affecting the hypothalamus through the nervous system because there is only one synaptic junction between pheromone receptors and the hypothalamus. Because sensory nerves are addressed to a specific location in the brain, this method has a highly specific drug effect, thereby greatly reducing the potential of undesirable side-effects.

VNO contact is important because the VNO is associated with chemoreceptive/pheromonal function. The VNO consists of a pair of blind tubular diverticula which are found at the inferior margin of the nasal septum. The VNO contains neuro-epithelia, the axons of which have direct synapses to the amygdala and from there, to the hypothalamus. The existence of the VNO has been well documented in most terrestrial vertebrates including the human fetus; however, in adult humans it is generally thought to be rudimentary (See Johnson, et al., surra).

Antifertility Activity

Figure 2:
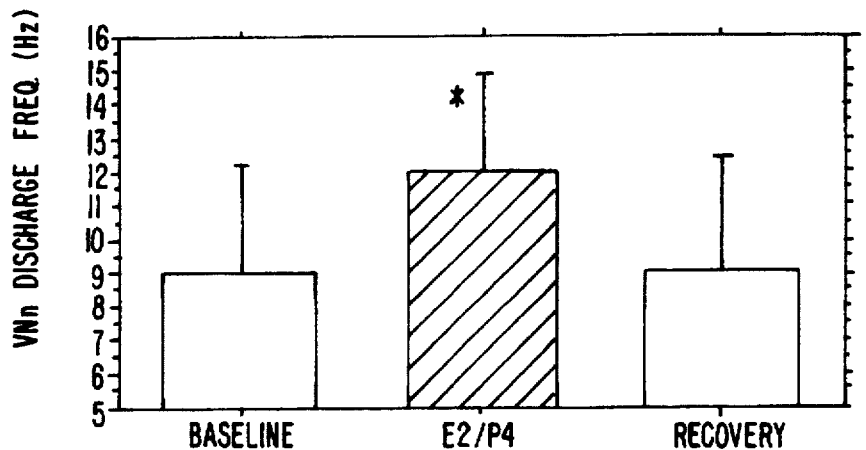
Figure 3:
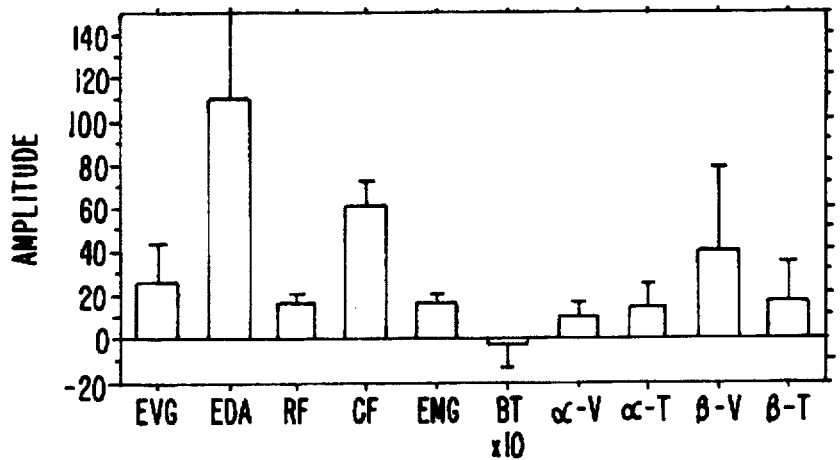
FIGS. 3 through 24 show the EVG, EDA, RF, CF, EMG, BT and EEG (alpha-V, alpha-T, beta-V and beta-T) data of administration of designated 19-nor-steroids in the VNO women.
Figure 4:
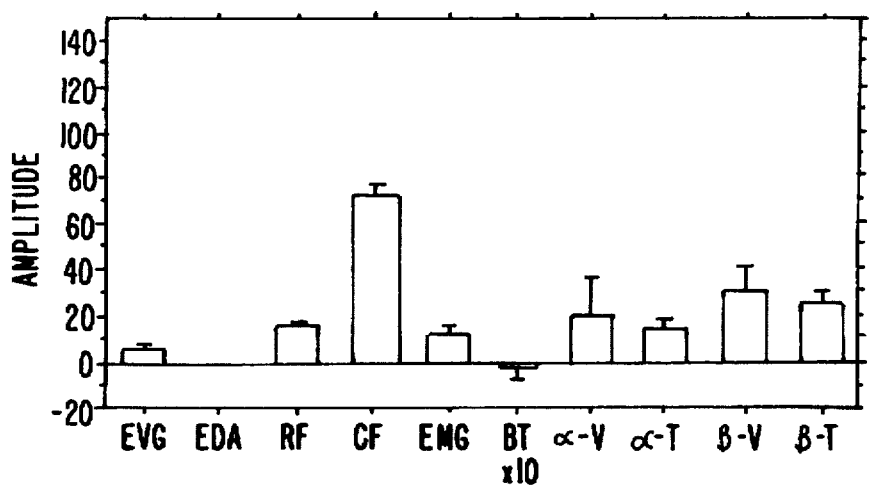
Figure 5:
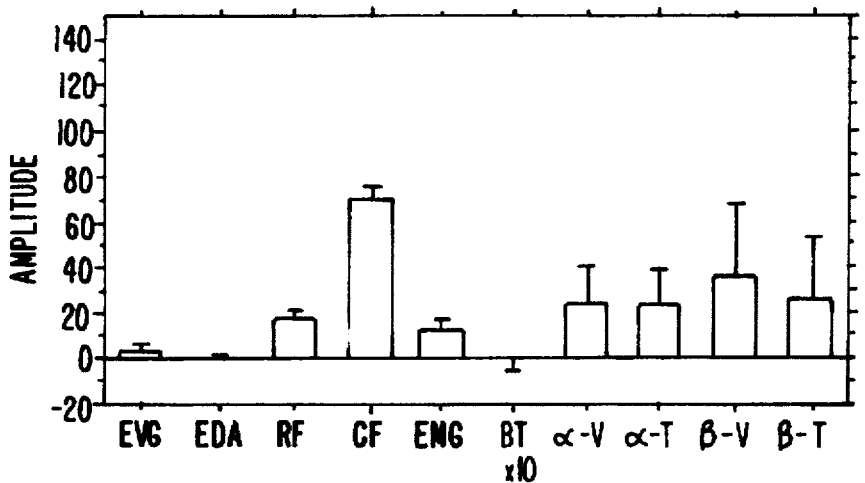
Figure 6:
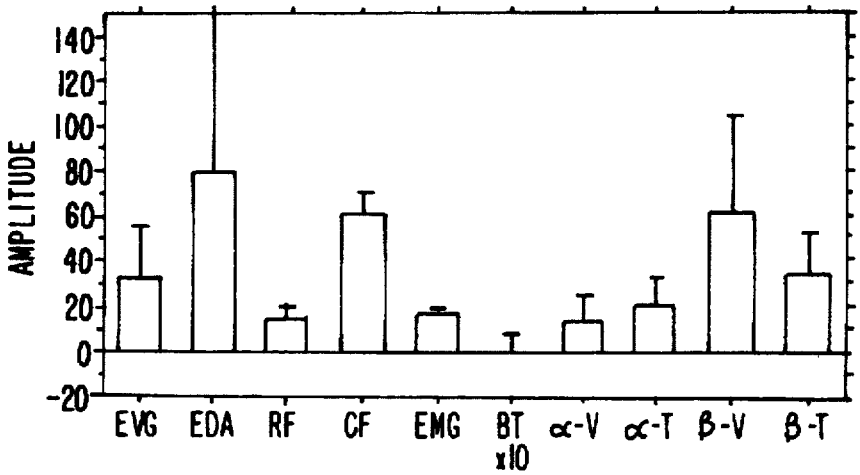
Figure 7:
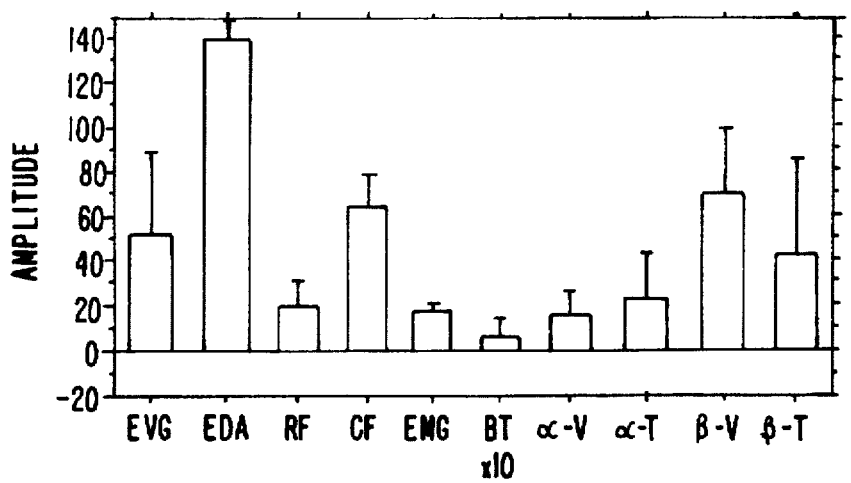
Figure 8:
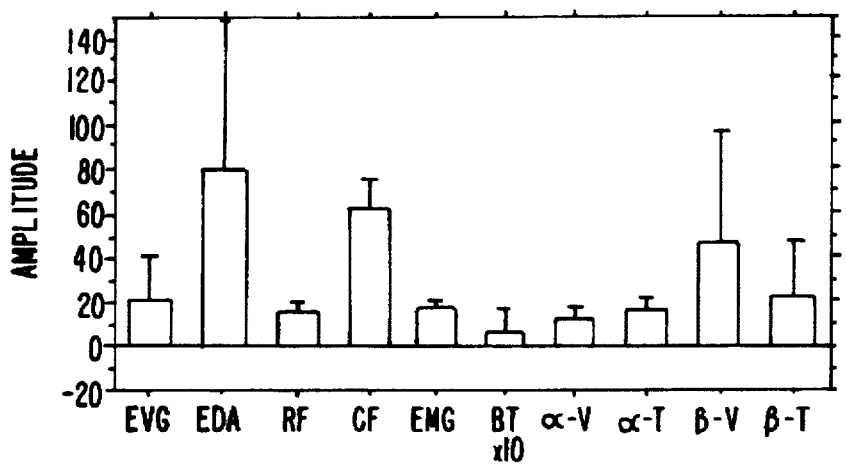
Figure 9:
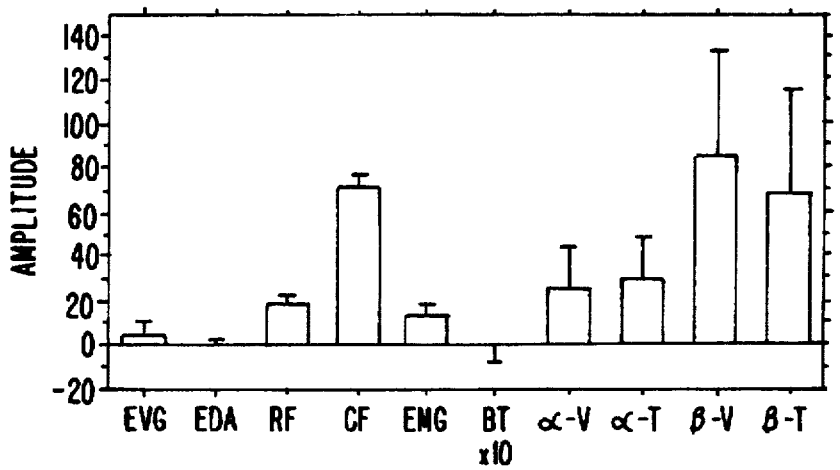
Figure 10:
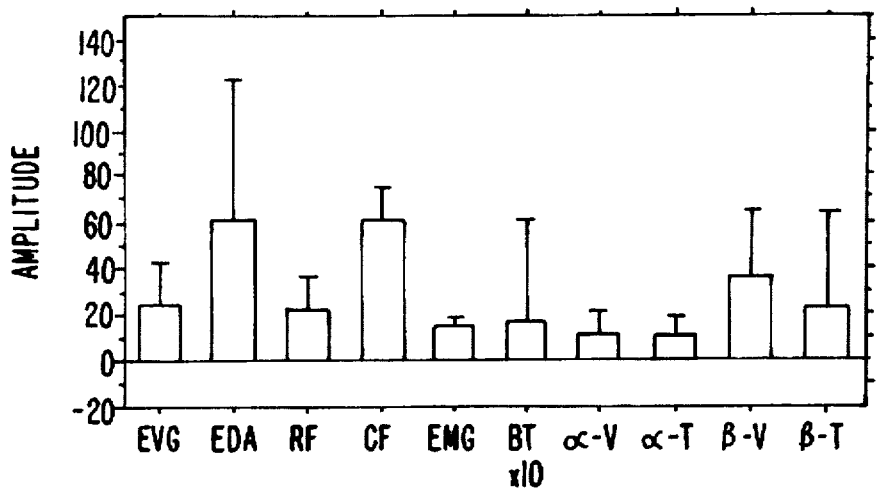
Figure 11:
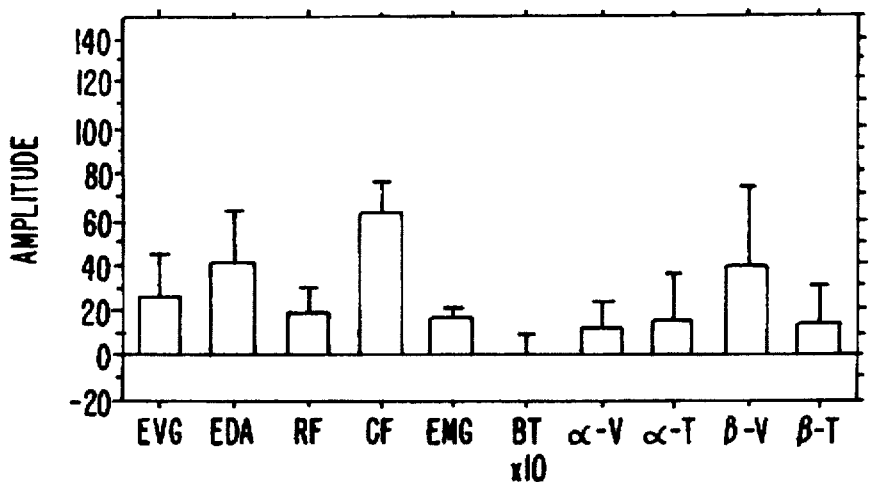
Figure 12:
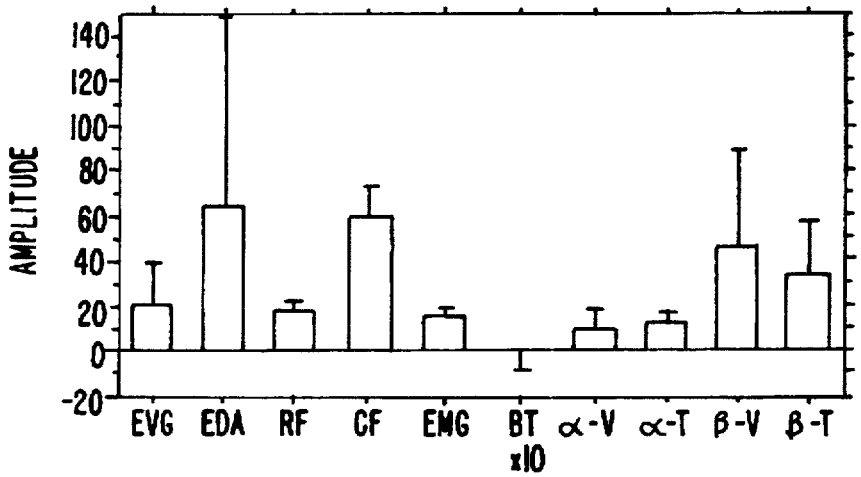
Figure 13:
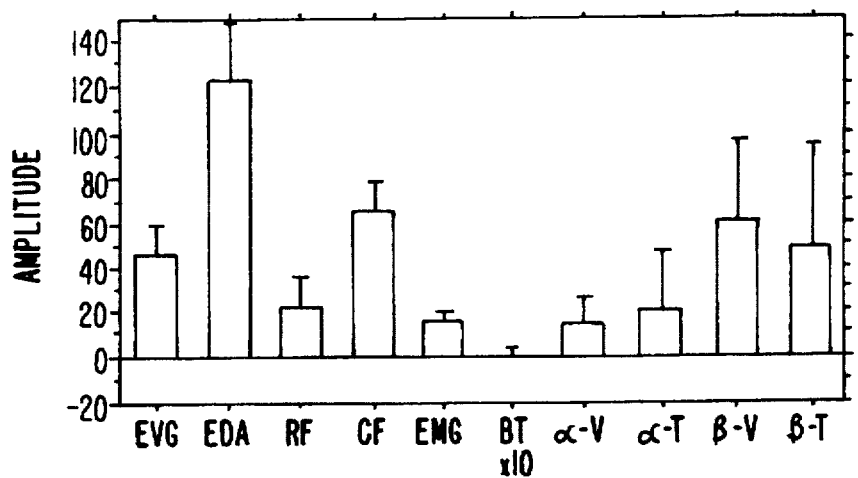
Figure 14:
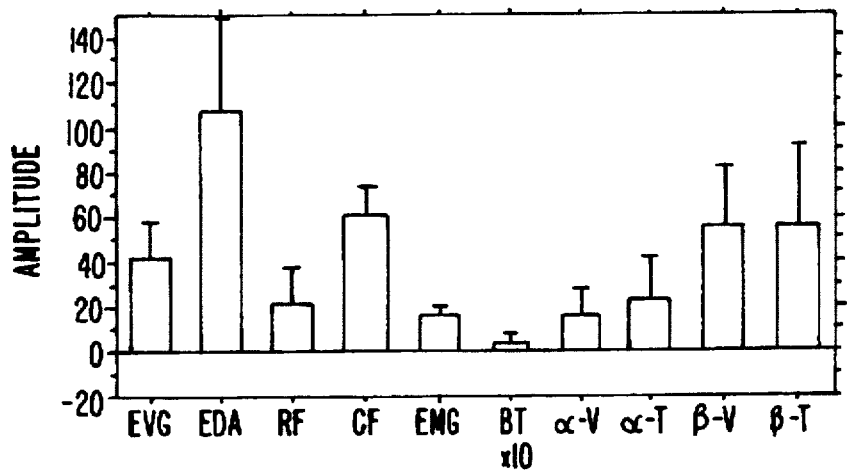
Figure 15:
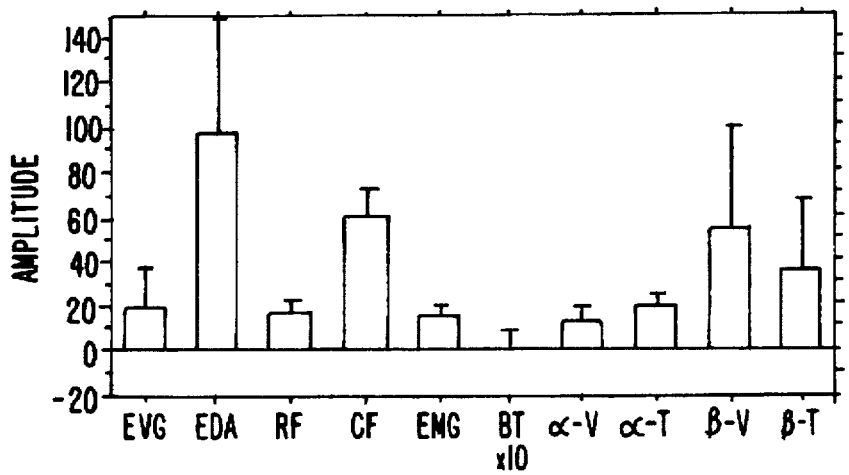
Figure 16:
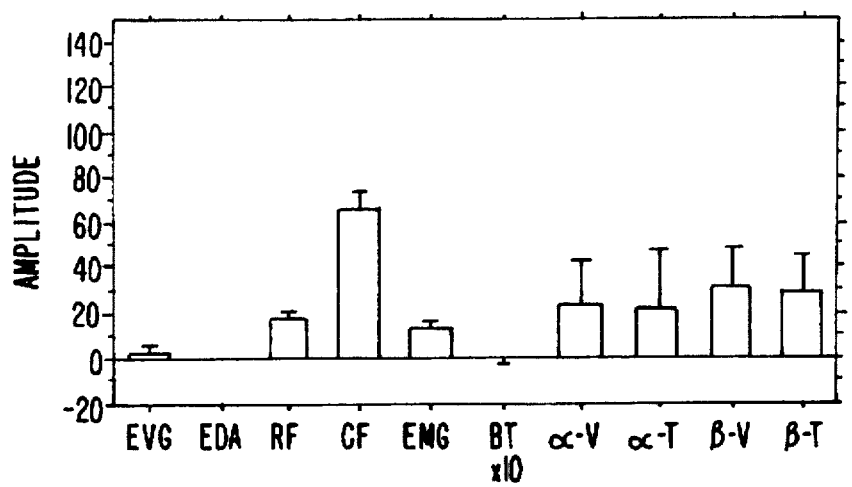
Figure 17:
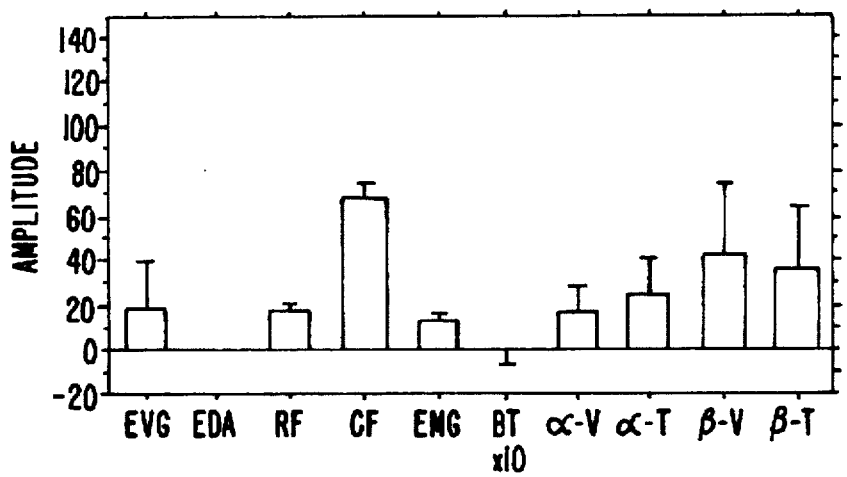
Figure 18:
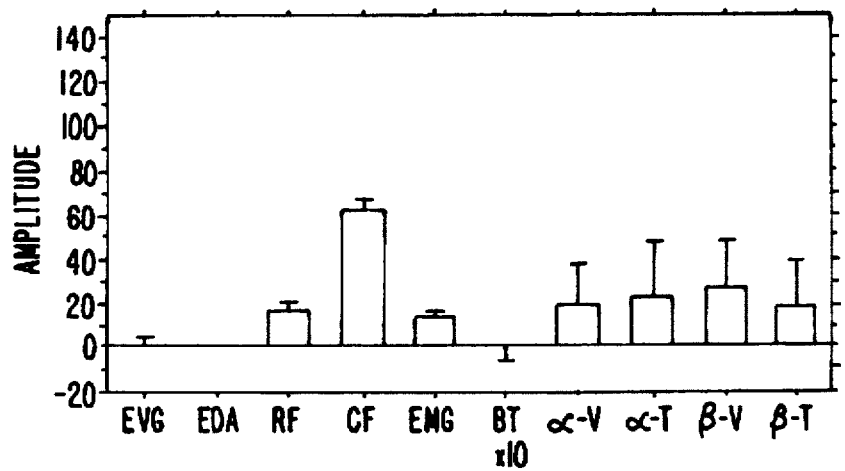
Figure 19:
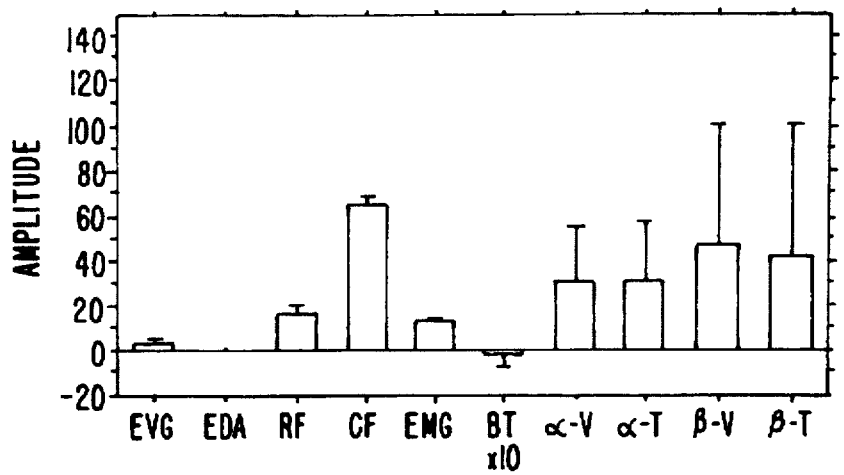
Figure 20:
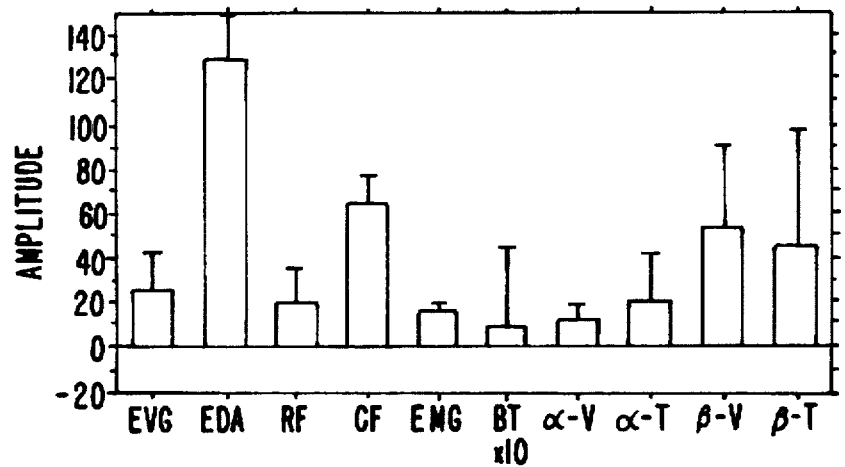
Figure 21:
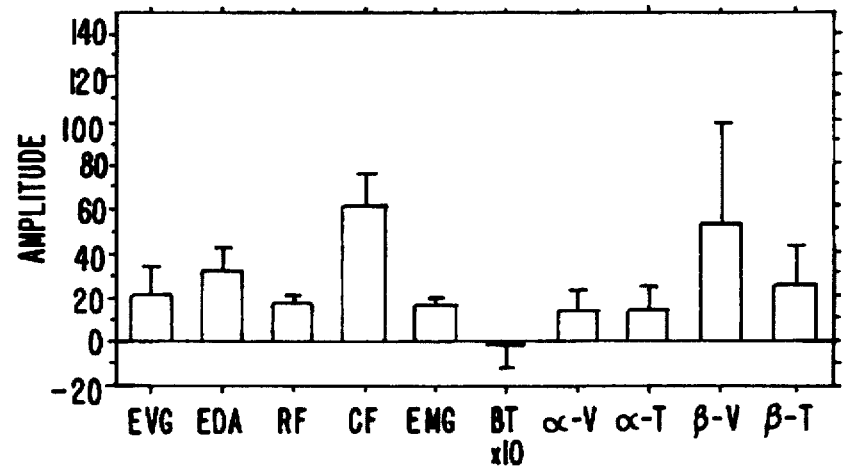
Figure 22:
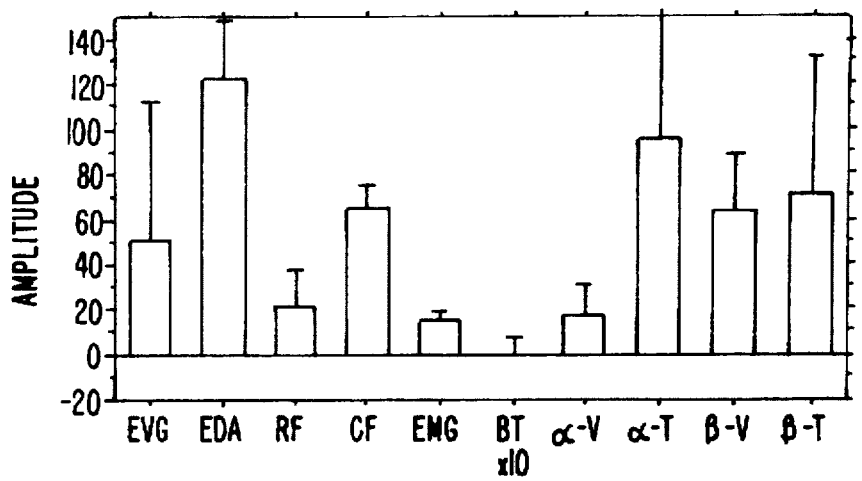
Figure 23:
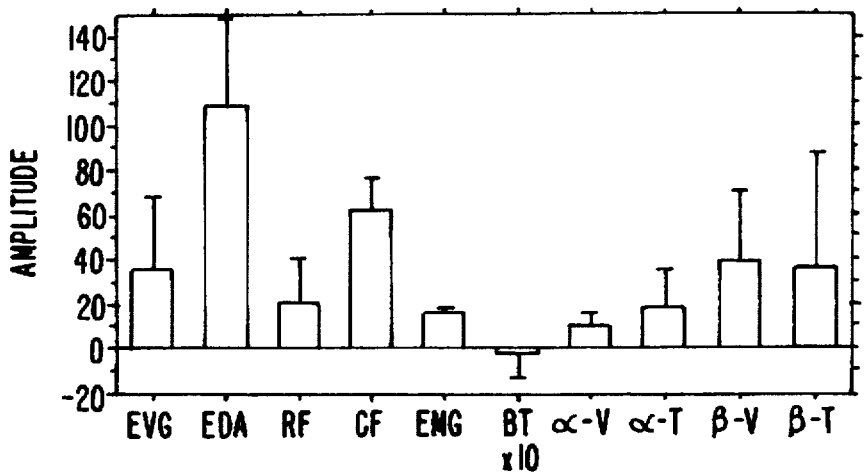
Figure 24:
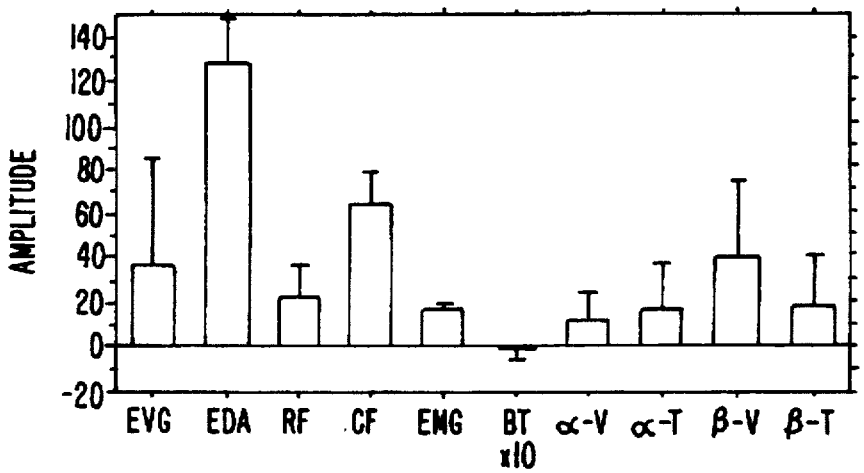
Figure 25:
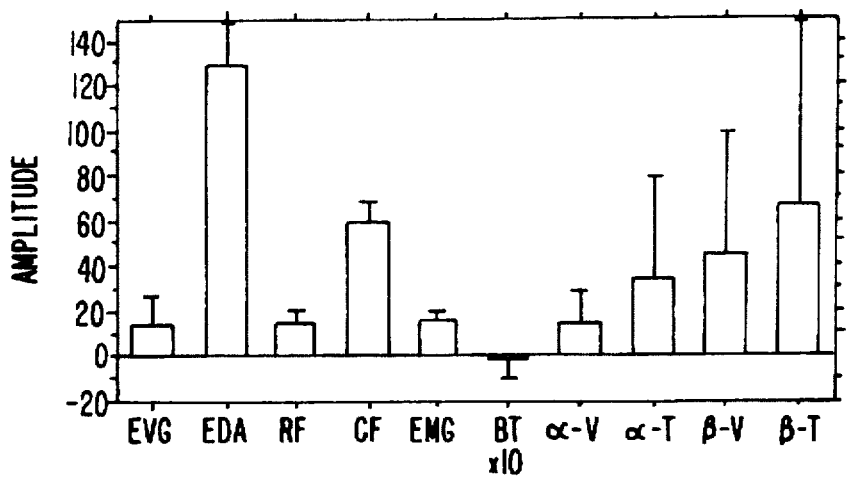
FIGS. 25 through 46 show the EVG, EDA, RF, CF, EMG, BT and EEG data of administration of designated 19-nor-steroids in the VNO of men.
Figure 26:
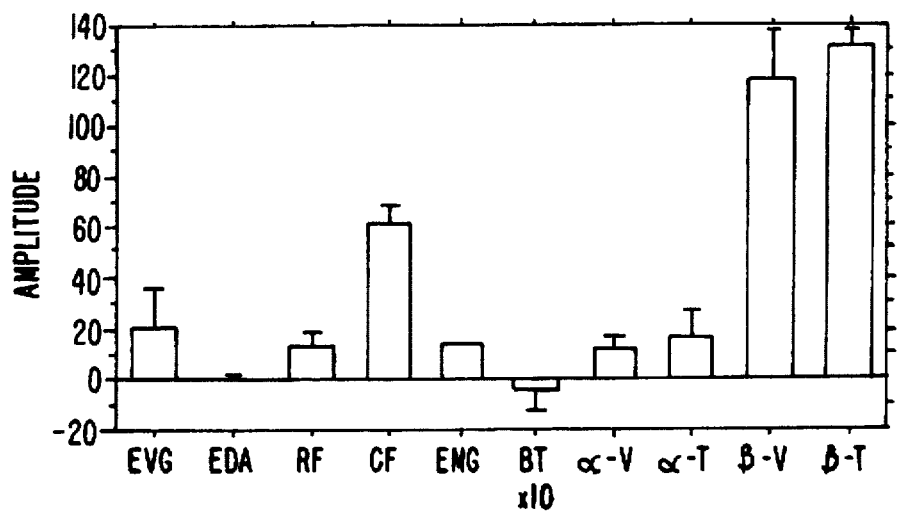
Figure 27:
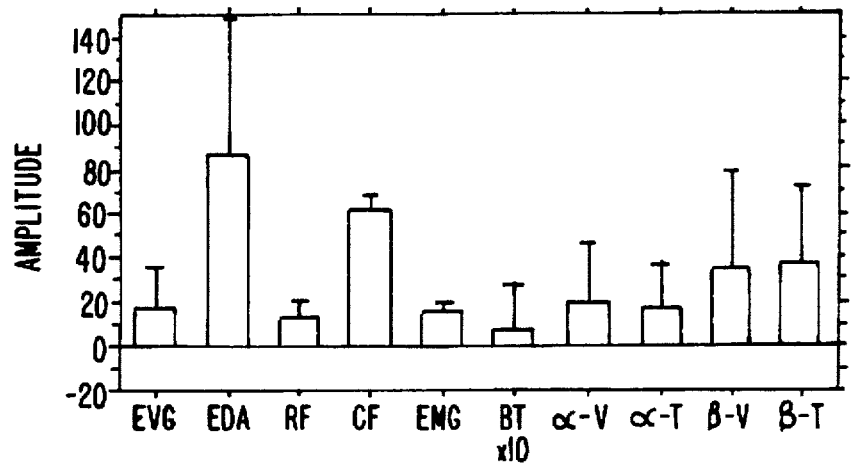
Figure 28:
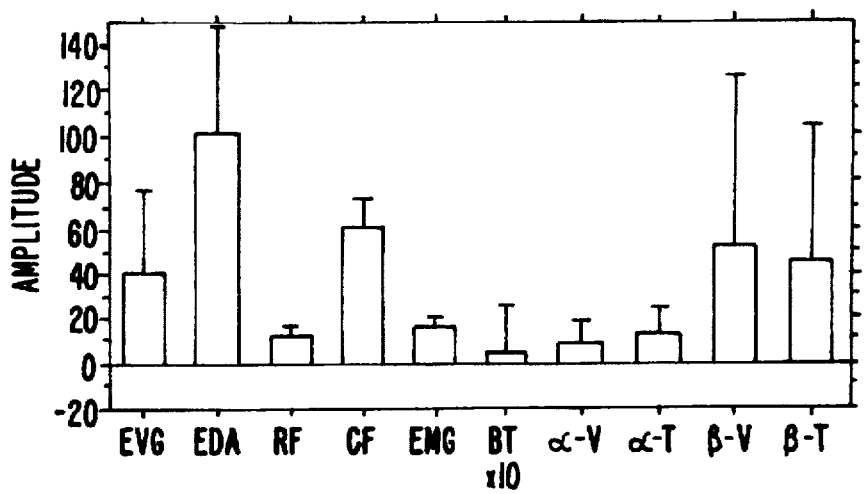
Figure 29:
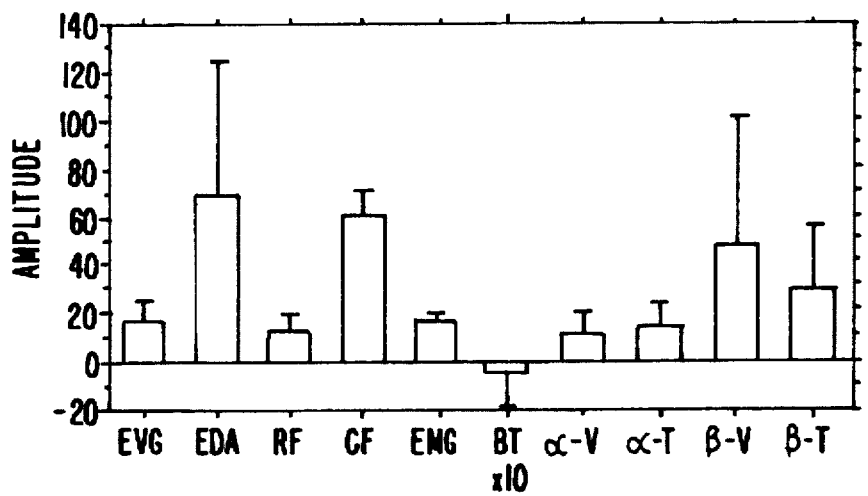
Figure 30:
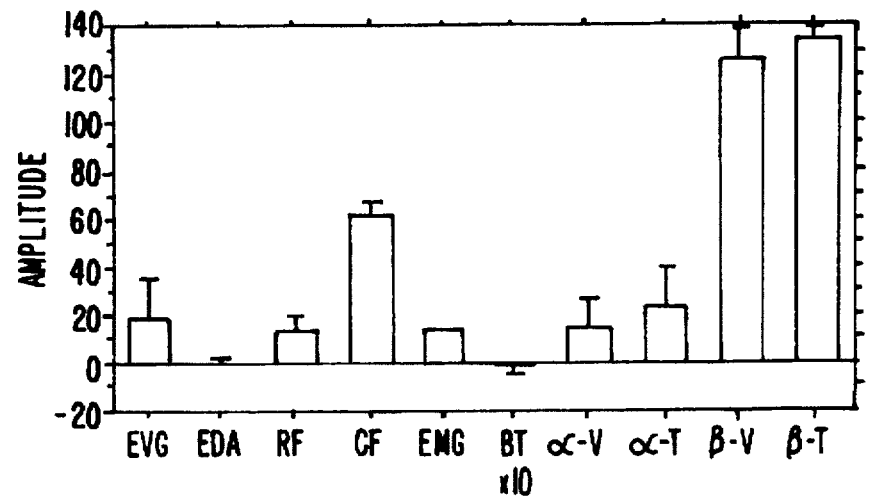
Figure 31:
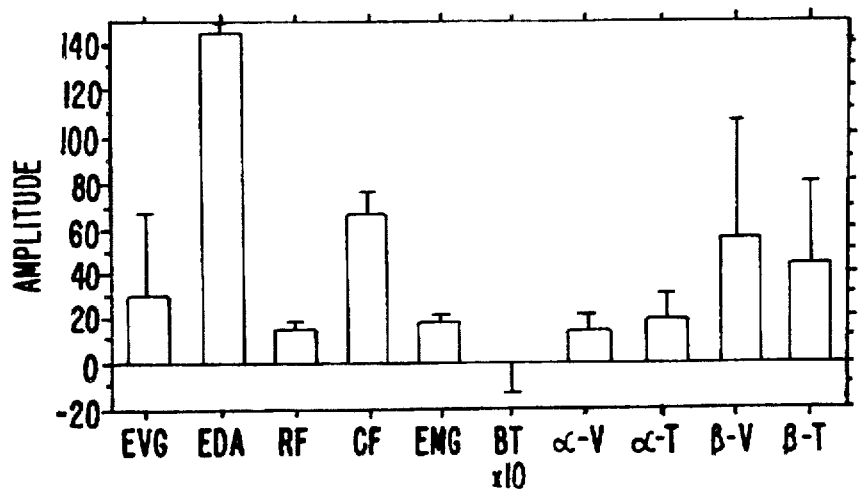
Figure 32:
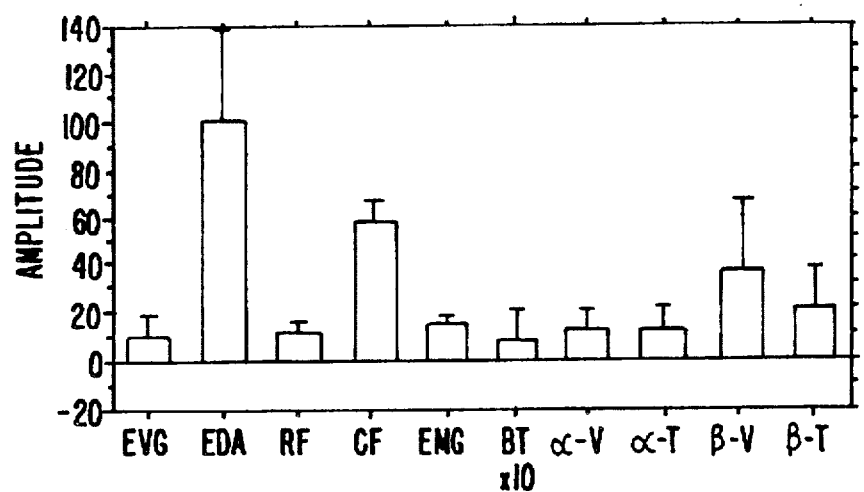
Figure 33:
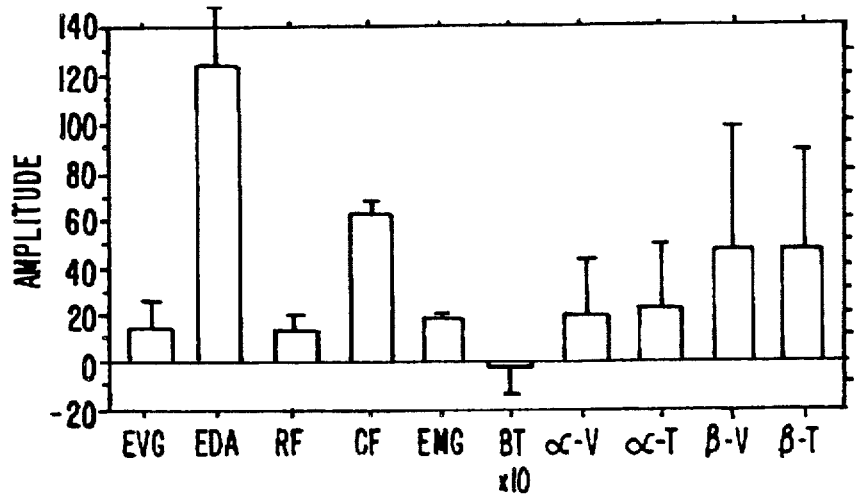
Figure 34:
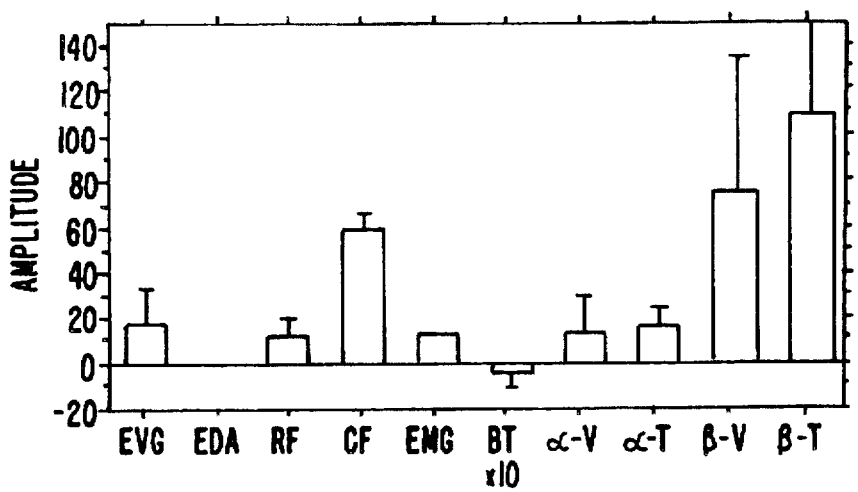
Figure 35:
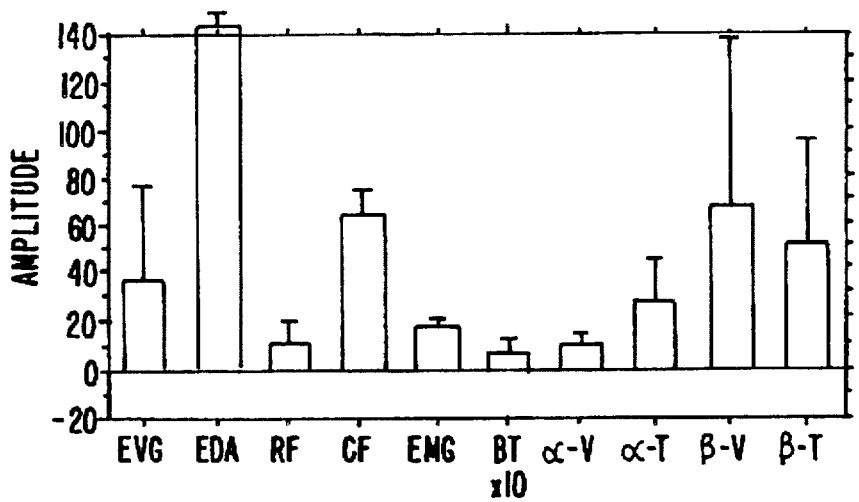
Figure 36:
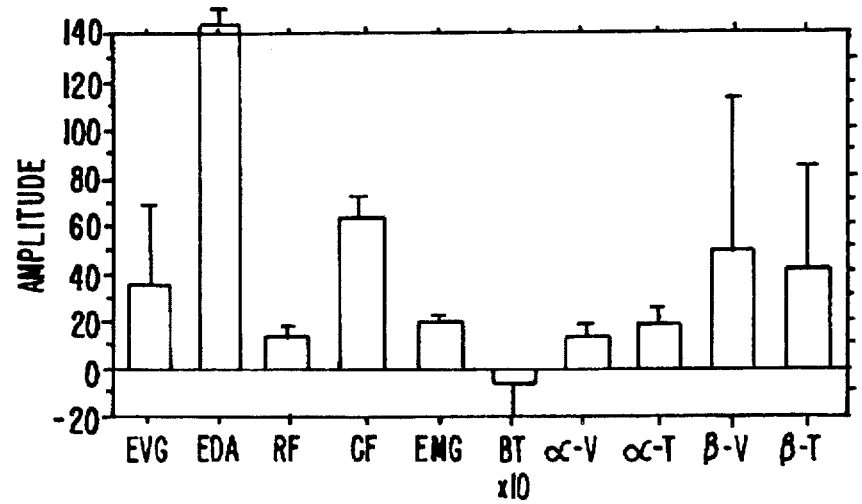
Figure 37:
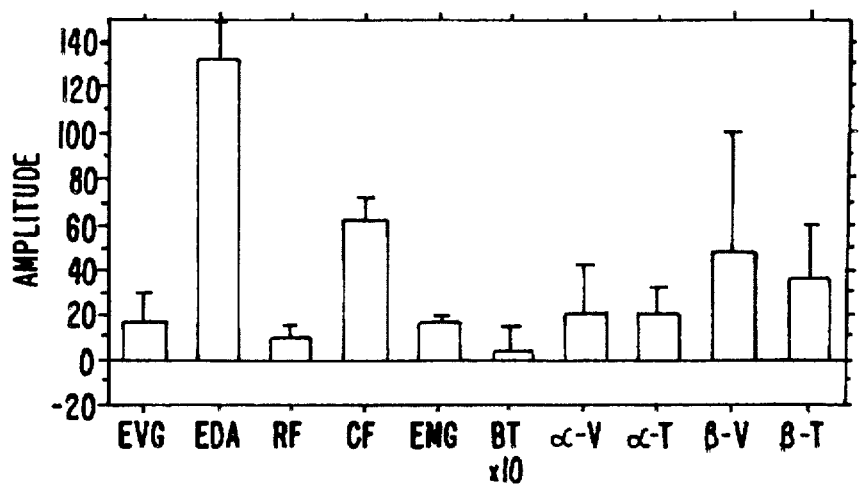
Figure 38:
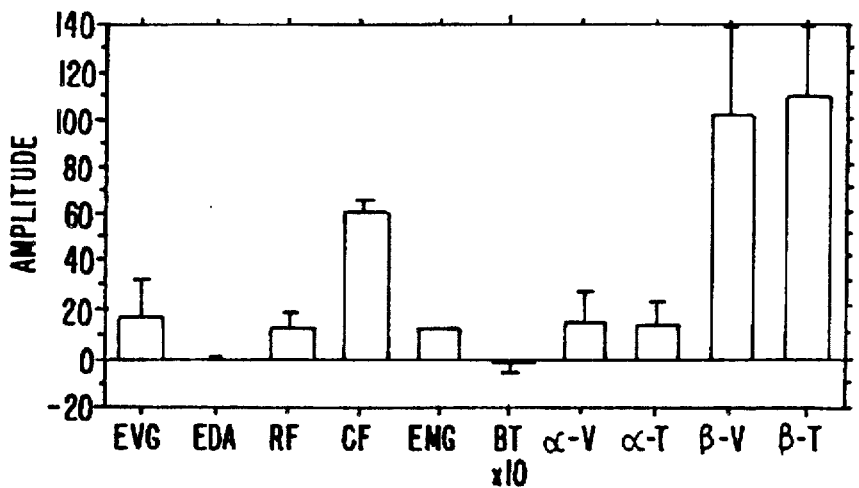
Figure 39:
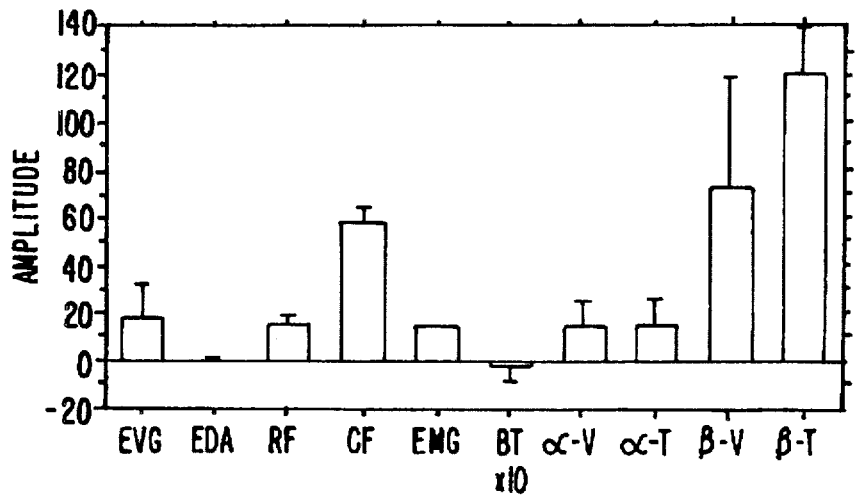
Figure 40:
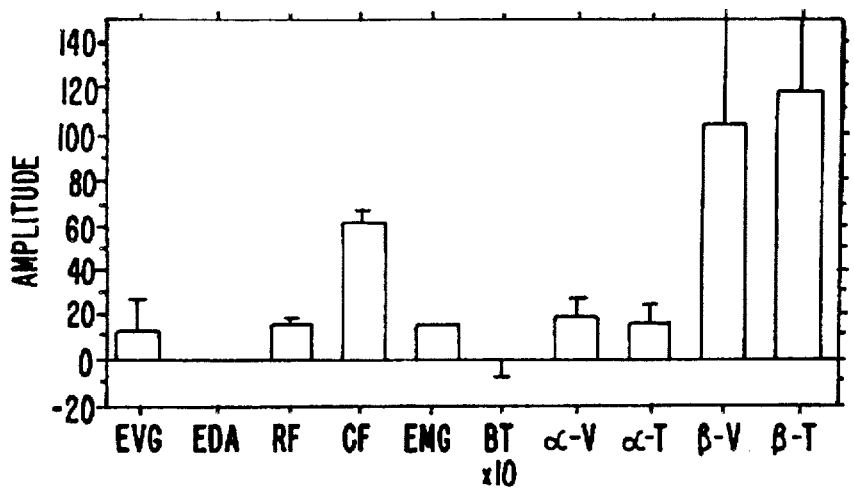
Figure 41:
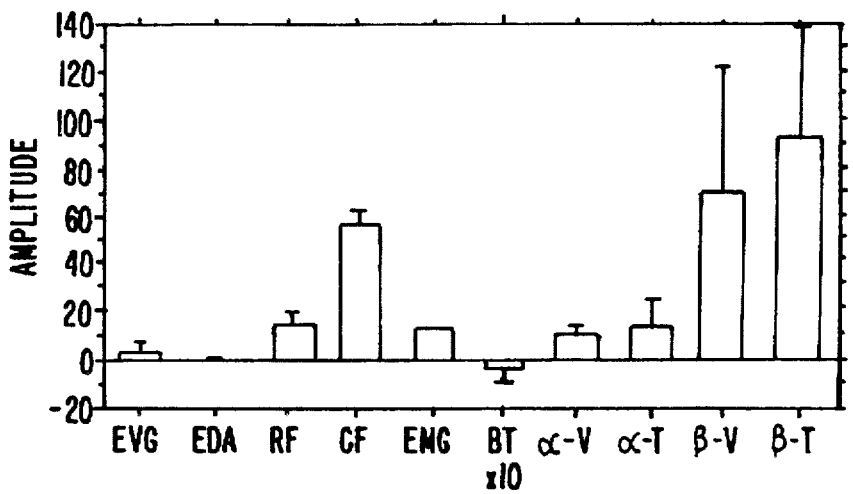
Figure 42:
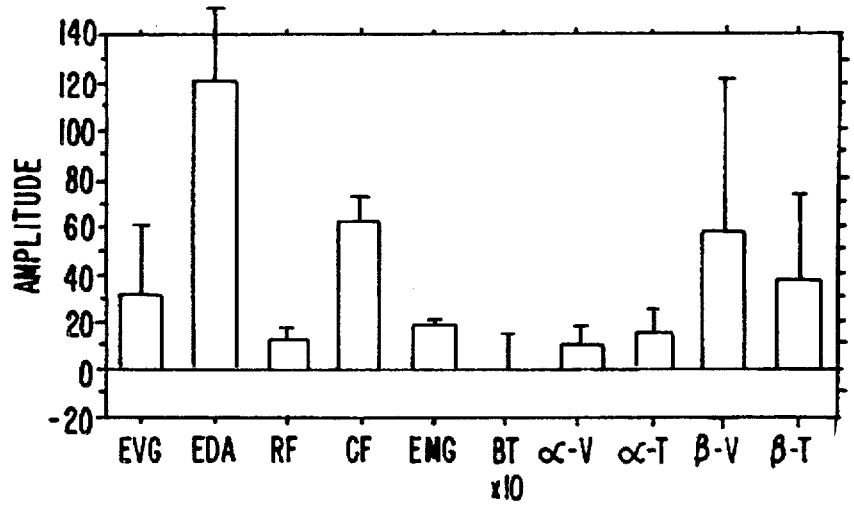
Figure 43:
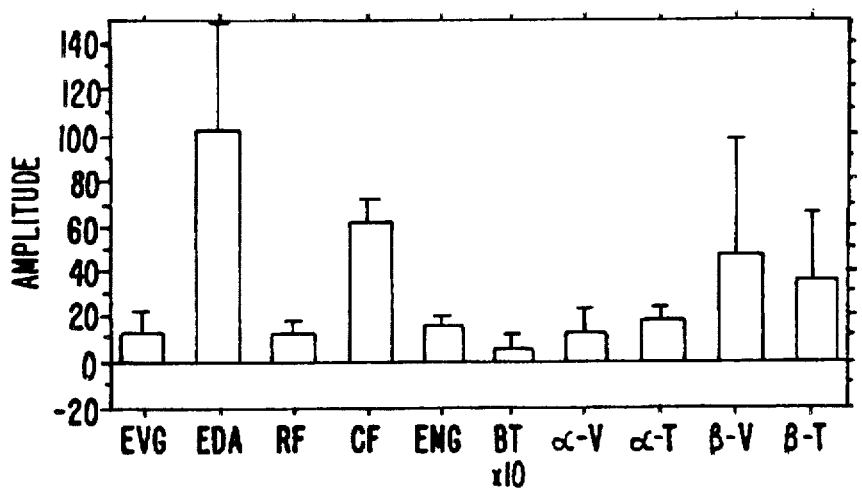
Figure 44:
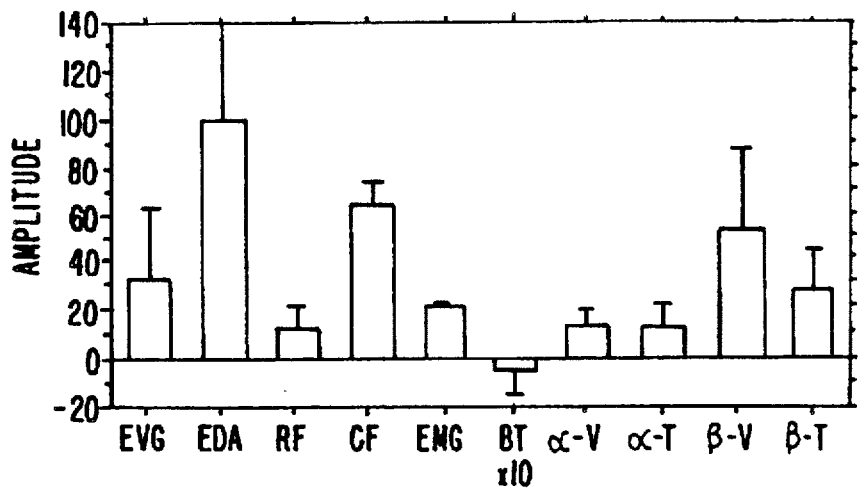
Figure 45:
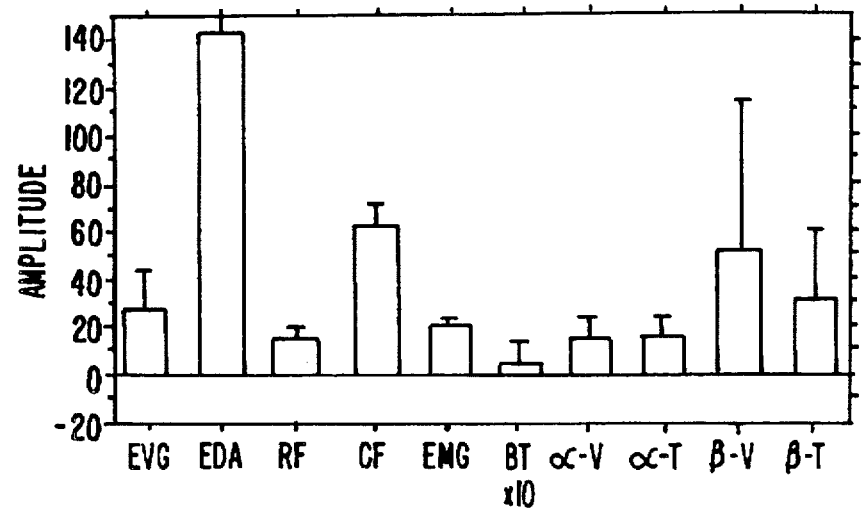
Figure 46:
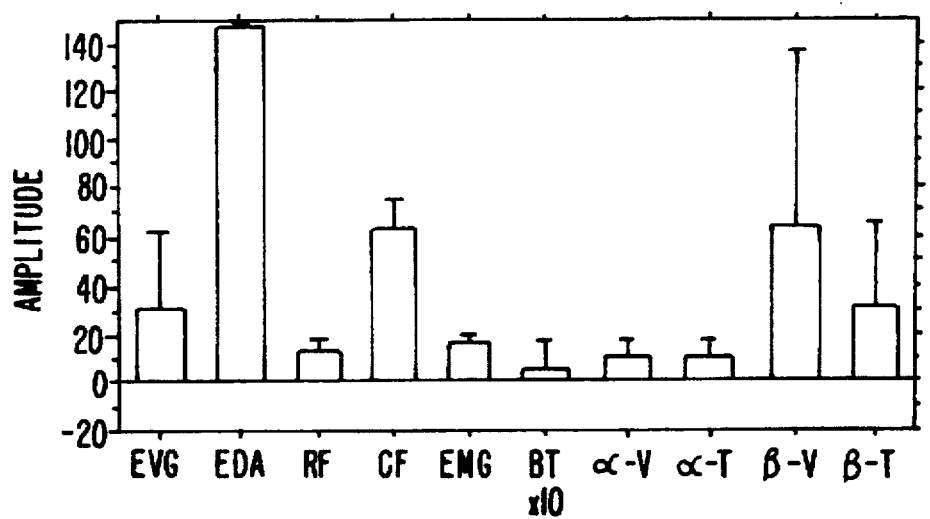

The steroid 19-norpregna-1,3,5(10)-trien-3-ol (compound E2/P4 in the 19-norpregnane chart) was tested in the VNO of female rats. The EVG and vomeronasal nerve (VNn) discharge frequency are shown in FIGS. 1 and 2, respectively. This data shows stimulation of the VNO. The steroid E2/P4 was shown to have postcoital antifertility activity when administered orally to female rats while having low hormonal activity (measured by estrogen-receptor binding). (Peters, et al., J. Med. Chem., 1989, 32,1642–52.) The data in FIGS. 1 and 2 suggest that this antifertility activity is explainable because E2/P4 is not a hormone, but acts as a vomeropherin through stimulation of the VNO, which in turn affects the hypothalamus. Consistent with the rat model data, the compound E2/P4 also shows VNO stimulation in women (see FIG. 22), and to a lesser extent, in men (see FIG. 44), and thus it is expected that the vomeropherins have antifertility activity in humans.

Stimulation of the hypothalamus via the VNO may allow one to suppress release of LH and FSH. This can provide a clinical method for treatment of prostatic cancer, precocious puberty (in males and females), endometriosis, uterine leiomyoma, breast cancer, premenstrual syndrome and disfunctional uterine bleeding.

The ligand substances described herein, or their sulfated cypionated, benzoated, proprionated, or glucuronated derivatives, may be administered directly, but are preferably administered as compositions. They are prepared in a liquid dosage form such as, for example, liquids, suspensions or the like, preferably in unit dosage forms suitable for single administration of precise dosages. Liquid dosages may be administered as nose drops or as an aerosol. Alternatively, the active compound can be prepared as a creme or an ointment composition and applied topically within the nasal cavity. In addition, a vomeropherin may be administered as vapor contained in an air puff delivered in the nasal cavity. As another alternative, delivery may occur by controlled release of these agents by encapsulation either in bulk or at a microscopic level using synthetic polymers, such as silicone, and natural polymers such as gelatin and cellulose. The release rate can be controlled by proper choice of the polymeric system used to control the diffusion rate (Langer, R. S. and Peppas, N. A., Biomaterials 2,201, 1981). Natural polymers, such as gelatin and cellulose slowly dissolve in a matter of minutes to hours while silicone remains intact for a period of months. The compositions will include a conventional pharmaceutical carrier or excipient, one or more of the active 19-nor-pregnane compound(s), and the composition may or may not additionally include one or more androstane or estrene steroids. In addition, the compositions may include other medicinal agents, pharmaceutical agents, carriers, adjuvants, etc.

The most likely means of communication of a semiochemical ligand is the inhalation of a naturally occurring pheromone present on the skin of another. It is estimated that the naturally occurring maximum concentration of a pregnane steroid on human skin is from 2 to 7 $ng/cm^2$. During intimate contact it is estimated that a human would be exposed to no more than 700 ng of a naturally occurring steroid. Since these compounds are relatively nonvolatile, it is estimated that, even during intimate contact, a human subject would inhale no more than 0.7 pg of a naturally occurring steroid from the skin of another. From the a count inhaled only about 1% would reach the receptors of the vomeronasal organ. Thus the estimated maximum natural exposure to naturally produced pheromones would be 0.007 pg.

The amount of vomeropherin administered will of course, be dependent on the subject being treated, the severity of the affliction, the manner of administration, the frequency of administration, and the judgment of the prescribing physician. However, a single dosage of at least about 10 picograms, delivered directly into the lumen of the vomeronasal organ, is effective in eliciting a transient autonomic response. When administered to the nasal cavity, the dosage is about 100 picograms to about 10 micrograms, preferably about 1 nanogram to about 10 micrograms, more preferably about 10 nanograms to 1 about microgram. The frequency of administration is desirably in the range of an hourly dose to a monthly dose, preferably from 8 times/day to once every other day, more preferably 1 to 3 times per day. Ointments containing one or more active compounds and optional pharmaceutical adjuvants in a carrier, such as, for example, water, saline, aqueous dextrose, glycerol, ethanol, and the like, can be prepared using a base such as, for example, petroleum jelly, lard, or lanolin.

Liquified pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Co., Easton, Pa., 15th Ed., 1975. The composition or formulation to be administered will, in any event, contain a quantity of one or more of the active compound(s) in an amount effective to alleviate the symptoms of the subject being treated.

For aerosol administration, the active ingredient is preferably supplied in finely divided form along with a surfactant and a propellant. Typical percentages of active ingredients are 0.001 to 2% by weight, preferably 0.004 to 0.10%.

Surfactants must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, olestearic and oleic acids with an aliphatic polyhydric alcohol or its cyclic anhydride such as, for example, ethylene glycol, glycerol, erythritol, arabitol, mannitol, sorbitol, and hexitol anhydrides derived from sorbitol (the sorbitan esters sold under the trademark "Spans") and the polyoxyethylene and polyoxypropylene derivatives of these esters. Mixed esters, such as mixed or natural glycerides, may be employed. The preferred surface-active agents are the oleates or sorbitan, e.g., those sold under the trademarks "Arlacel C" (sorbitan sesquioleate), "Span 80" (sorbitan monoleate) and "Span 85" (sorbitan trioleate). The surfactant may constitute 0.1–20% by weight of the composition, preferably 0.25–5%.

The balance of the composition is ordinarily propellant. Liquified propellants are typically gases at ambient conditions, and are condensed under pressure. Among suitable liquefied propellants are the lower alkanes containing up to five carbons, such as butane and propane; fluorinated or fluorochlorinated alkanes, such as are sold under the trademark "Freon". Mixtures of the above may also be employed.

In producing the aerosol, a container equipped with a suitable valve is filled with the appropriate propellant, containing the finely divided active ingredient and surfactant. The ingredients are thus maintained at an elevated pressure until released by action of the valve.

Yet another means of administration is topical application of a volatile liquid composition to the skin, preferably facial skin, of an individual. The composition will usually contain an alcohol such as ethanol or isopropanol. A pleasant odorant may also be included in the composition.

Measuring Affect, Mood and Character Trait

Feeling states associated with affects, moods and character traits are generally measured by use of a questionnaire. For example questionnaires comprising a number of adjectives which refer to feeling states may be administered to an individual. The individual evaluates his or her feeling state described by the adjective and rates the intensity of the feeling on a numerical scale. Clustering of re lated adjectives and statistical analysis of a subject's evaluation of each adjective provides a basis for the measurement of various feeling states.

Alternatively, feeling states may be measured by autonomic changes, such as those used in polygraphic evaluations (galvanic skin response, pulse rate and the like). Cabanac, M. Annual Review of Physiology (1975) 37:415; Hardy, J. D., "Body Temperature Regulation", Chapter 59, pp. 1417. In: Medical Physiology. Vol. II Ed.: VB Mountcastle (1980); Wolfram Bouscein. Electrodermal Activity (Plenum Press 1992). In addition, non-verbal cues such as facial expression and body posture may be evaluated.

EXAMPLES

The following examples are intended to illustrate but not to limit the invention.

Abbreviations used in the examples are as follows: aq.= aqueous; RT.=room temperature; PE=petroleum ether (b.p. 50°–70°); DMF=N,N-dimethylformamide; DMSO= dimethyl sulfoxide; THF=tetrahydrofuran.

Scheme 1. Syntheses of 19-norpregnanes

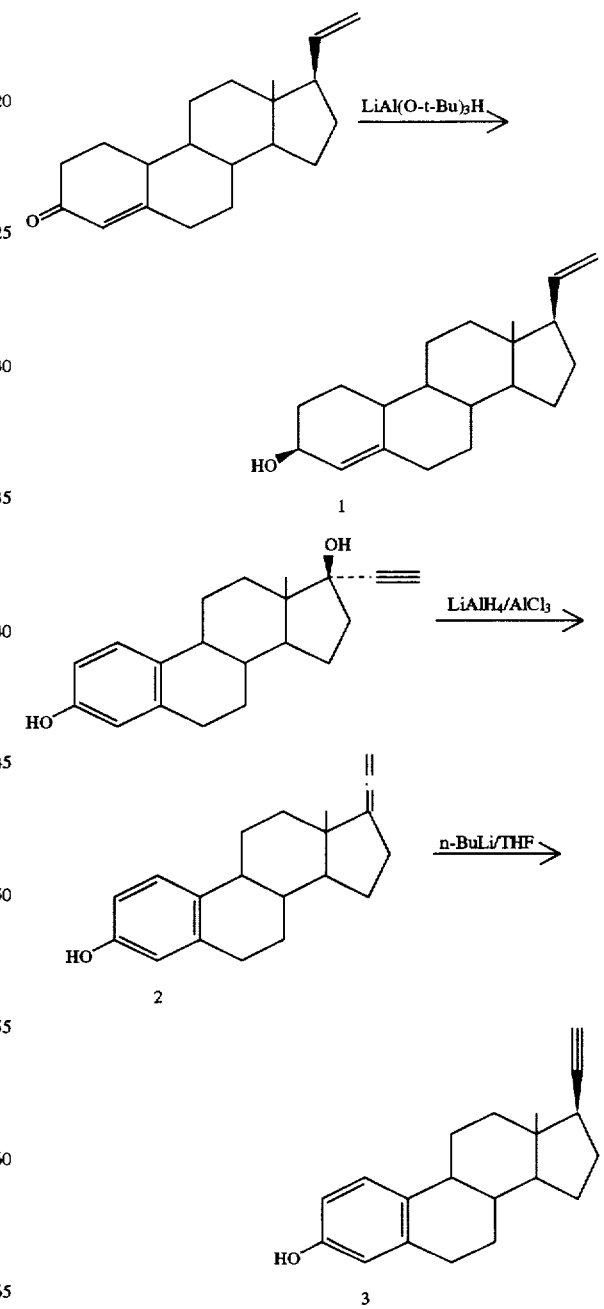

43
-continued
Scheme 1. Syntheses of 19-norpregnanes
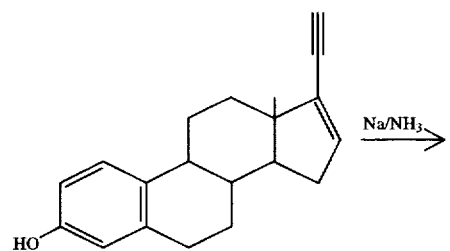
Scheme 3. Further syntheses of norpregnanes
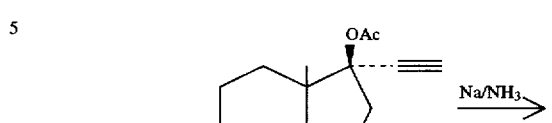
Scheme 2. Syntheses of further norpregnanes.
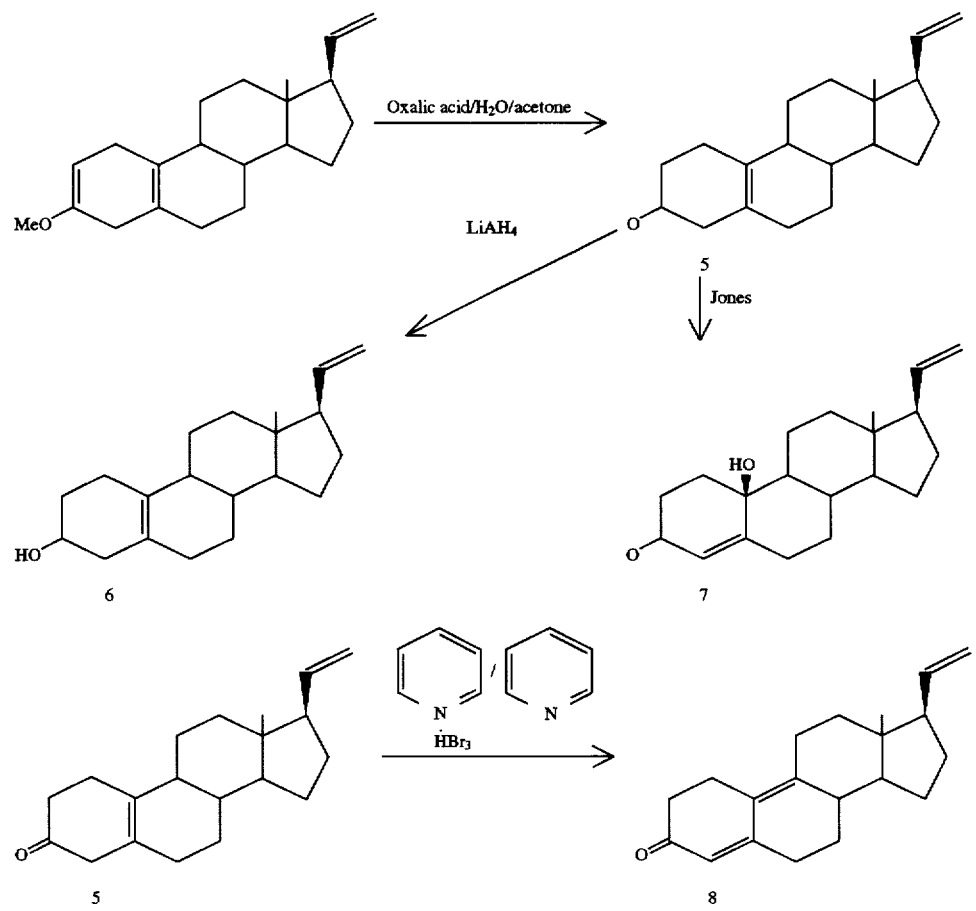

Scheme 3. Further syntheses of norpregnanes

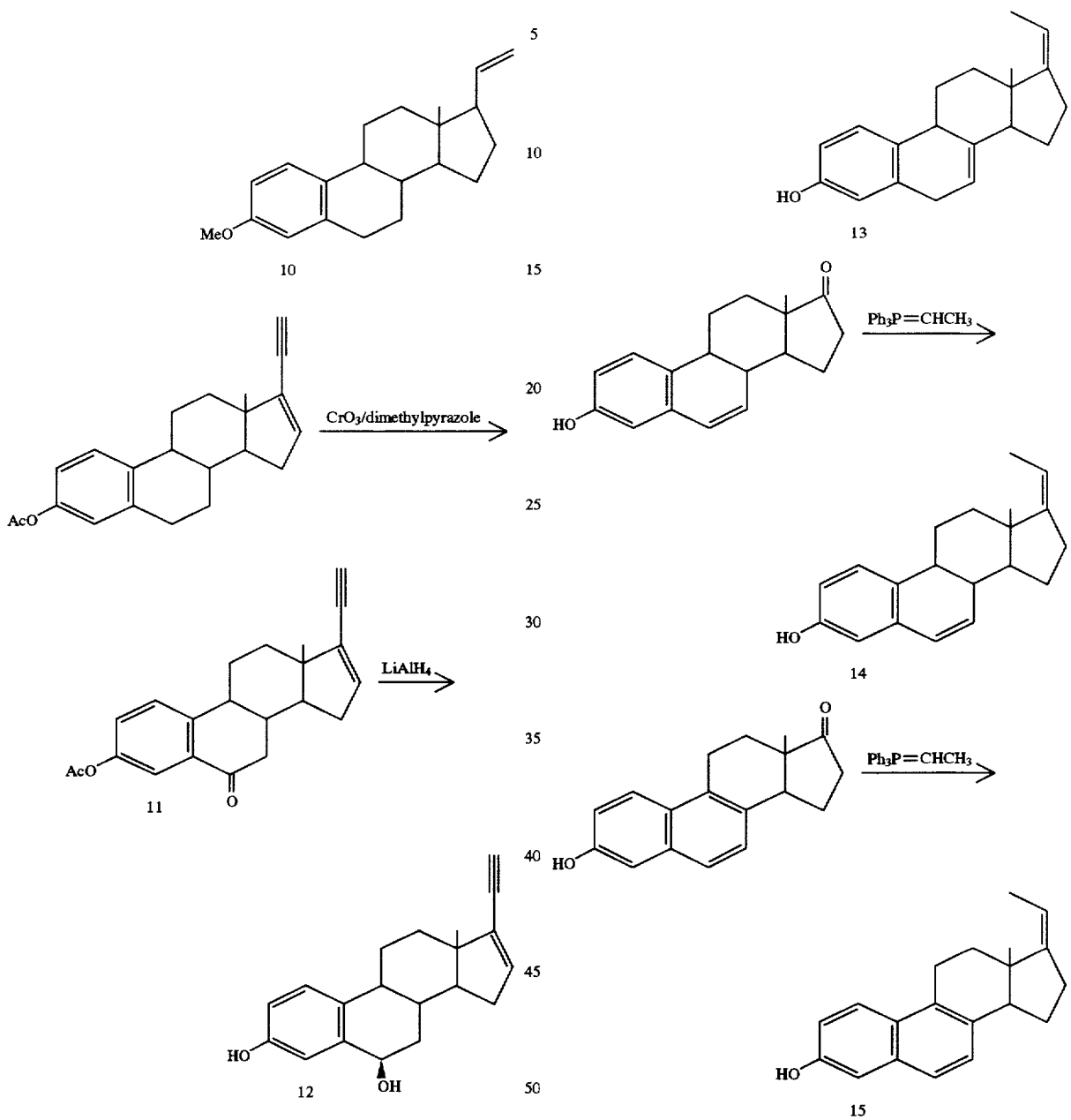

Scheme 4. 17-Ethylenation of ketones

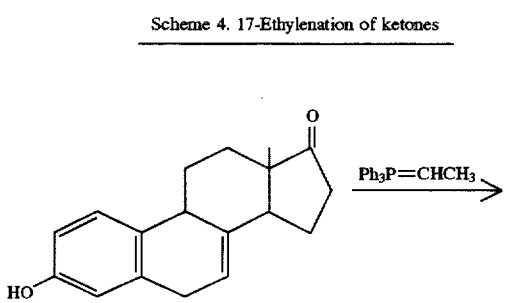

Example 1

19-Norpreana-4,20-dien-3β-ol, 1: A suspension of 19-norpregna4,20-dien-3-one (0.38 g, 13 mmhl) and lithium tri-t-butoxyaluminohydride (1.36 g, 5.35 mmol) in 20 mL of anh. ether was stirred 5 h at room temperature, following which Glauber's salt (6.74 g) was added. The resulting mixture was stirred 5 mn. and then filtered through a glass frit. The residue was washed with 5 20 mL portions of ether and the combined filtrates were concentrated under reduced pressure. The crude product was purified by preparative TLC on silica gel GF using 5% ethyl acetate/methylene chloride as eluent to give a yellow resin (39.6 mg, 0.138 mmol, 11%) homogeneous to TLC (5% ethyl acetate/methylene chloride on silica gel; $R_f$ 0.29).

Example 2

19-Norpregna-1,3,5(10),17,20-pentaen-3-ol, 2: To a suspension of lithium aluminum hydride (LAH, 256.1 mg, 6.748 mmcl) and aluminum chloride (296.8 mg, 2.227 mmol) in 20 mL of anh. ether under argon was added ethinylestradiol (1.0000 g, 3.3738 mmol) in 20 mL anh. ether. After refluxing 20 h the reaction was quenched with the addition of Glauber's salt (2.00 g) and s stirring a further 2 h. The mixture was then filtered through diatomaceous earth and the residue was washed with 3 10 mL portions of ethyl acetate. Concentration of the combined filtrates, flash chromatography on silica gel with 15% ethyl acetate/hexanes, and twofold recrystallization from aqueous ethanol gave slightly tan needles (367.5 mg, 1.311 mmol, 39%), m.p. 132°–1330° C., homogeneous to TLC (20% ethyl acetate/hexanes on silica gel; $R_f$ 0.36; estra-1,3,5(10), 16-tetraen-3-ol $R_f$ 0.36).

Example 3

19-Norpregna-1,3,5(1)-trien-3-ol-20β-yne, 3: To a cooled (dry ice/acetone bath) solution of 19-norpregna-1,3,5(10), 17,20-pentaen-3-ol (2, 280.4 mg, 1.000 mmol) in 28 mL of anh. THF under argon was added n-BuLi (2.5M in hexane, 1.2 mL, 3.0 mmol) over 10 min. Stirring was continued for 18 h, during which the reaction was allowed to gradually warm to RT. The reaction was quenched with 25 mL of 1N HCl and then extracted with 3 10 portions of ether. The combined organic extracts were washed with 25 mL of saturated sodium bicarbonate+25 mL of brine, dried over magnesium sulfate, and filtered through diatomaceous earth. The reside was washed with 10 mL of ether and the combined filtrates were concentrated under reduced pressure. Flash chromatography of the resulting yellow resin on silica gel with 20% ethyl acetate/hexanes, followed by recrystallization from aqueous ethanol gave fine, white needles (150.5 mg, 0.5367 mmol, 54%), m.p. 148°–149° C., homogeneous to TLC (20% ethyl acetate/hexanes on silica gel; $R_f$ 0.34; starting material $R_f$ 0.37).

Example 4

19-Norpregna-1,3,5(10),16,20-pentaen-3-ol, 4: 19-Norpregna-1,3,5(10),16-tetraen-3-ol-20-yne (200.0 mg, 0.7184 mmol) in 9 mL anh. THF was added to approx. 30 mL of anh. ammonia. Sodium (0.07 g, 3 mg-atom) was added in small pieces and the reaction was stirred 1 h, during which the color disappeared. Abs. ethanol (3 mL) was added and the mixture was allowed to warm to RT overnight. HCl (1N, 20 mL) was added the mixture was extracted three times with 10 mL portions of methylene chloride. The combined organic extracts were washed with 10 mL of brine, dried over magnesium sulfate, and filtered through diatomaceous earth. The reside was washed with 10 mL of methylene chloride and the combined filtrates were concentrated under reduced pressure. Preparative TLC (silica gel GF, with 20% ethyl acetate/hexanes) of the resulting amber resin, followed by recrystallization from benzene/hexanes gave an off-white powder, m.p. 123°–125° C. TLC (20% ethyl acetate/hexanes) showed a major product ($R_f$ 0.38) with a minor contaminant ($R_f$ 0.04).

Example 5

19-Norpregna-5(10), 20-dien-3-one, 5: 19-Norpregna-2,5(10),20-trien-3-yl methyl ether (750.0 mg, 2.513 mmol) was dissolved in 80 mL of acetone and oxalic acid (0.88g, 7.0 mmol) in 12 mL of water was added. Further acetone (20 mL) was added to bring most of the precipitate back into solution and the reaction was stirred 6 h. Following saturated sodium bicarbonate quench (30 mL) the reaction mixture was twice with 40 mL portions of ethyl acetate. The combined organic extracts were washed twice with 50 mL portions of brine, dried over magnesium sulfate, and filtered through diatomaceous earth. The reside was washed with 25 mL of ethyl acetate and the combined filtrates were concentrated under reduced pressure. Flash chromatography (10% ethyl acetate/hexanes on silica gel) gave a colorless resin (0.54 g, 1.9 mmol, 76%).

Example 6

19-Norpregna-5(10),20-dien-3-ol, 6: To an ethereal (8.4 mL) solution of 19-norpregna-5(10),20-dien-3-one (0.42 g, 1.5 mmol) was added 69.7 mg (1.84 mmol) of LAH and the reaction was stirred 30 min. Glauber's salt (2.79 g) was added and the suspension was stirred an additional 10 mL. The mixture was then filtered through diatomaceous earth and the residue was extracted with 435 mL portions of ether. The combined filtrates were concentrated under reduced pressure and the resulting oil was flash chromatographed (20% ethyl acetate/hexanes on silica gel) to give an off-white foam (0.38 g, 1.3 mmol, 88%).

Example 7

19-Norpregna-4,20-dien-10β-ol-3-one, 7: 19-Norpregna-5(10),20-dien-3-one (5,0.45 g, 1.6 mmol) in DMF (5.7 mL) was cooled in an ice-acetone bath and Jones reagent (2.67 M, 0.19 mL, 0.51 mmol) was added. After stirring 1½ h a further 0.19 mL of Jones reagent were added. Stirring was continued 45 min., after which 0.38 mL of Jones reagent were added. The reaction was quenched after stirring 1 more hour by the addition of 2-propanol (0.38 mL). Ethyl acetate (100 mL) was added and the mixture was washed with 3 50 mL portions of water+50 mL of brine, dried over magnesium sulfate, and filtered through diatomaceous earth. The residue was washed with 10 mL of ethyl acetate and the combined filtrates were concentrated under reduced pressure. Preparative TLC on alumina with 50% ethyl acetate/hexanes gave a white, crystalline film (89.2 mg, 0.297 mmol, 19%). TLC (50% ethyl acetate/hexanes on silica gel) showed mostly produce ($R_f$ 0.46), contaminated with a little starting material ($R_f$ 0.73).

Example 8

19-Norpregna-4,9(10), 20-trien-3-one, 8: A solution of 19-Norpregna-5(10),20-dien-3-one (0.34 g, 1.2 mmol) in anh. Pyridine (4.0 mL, 49 mmol) was cooled in an ice-salt bath to below −8° C. and solid pyridinium bromide perbromide (1.26 g, 3.94 mmol) was added at such a rate that the reaction temperature did not exceed −2° C. After stirring 1 min., 0.20 g of phenol were added, the cold bath was removed, and the reaction was stirre at RT for 24 h. Ethyl acetate (50 mL) was added and the mixture was washed with 50 mL of 1N HCl+25 mL of saturated CuSO$_4$+25 mL of 5% sodium hydroxide+25 mL of water+25 mL of brine. The mixture was then dried over sodium sulfate for 4 h and afterwards filtered through a glass frit. The residue was washed with 10 mL of ethyl acetate and the combined filtrates were concentrated under reduced pressure. The resulting dark syrup (512.8 mg) was taken up in 8 mL of abs. ethanol, zinc dust (260.8 mg, 3.990 mg-atom) was added, and the suspension was refluxed ½ h. The reduction mixture was filtered through cotton and the residue was washed with 10 mL of ethanol. Concentration of the combined filtrates and two-fold purification by preparative TLC, first on silica gel GF (1000 μ, 20% ethyl acetate/hexanes as eluent) then on alumina GF (1000 μ, 20% ethyl acetate/hexanes), gave a nearly colorless resin (152.8 mg, 0.5410 mmol, 45%) homogeneous to TLC ($R_f$ 0.22, 10% ethyl acetate/hexanes on silica gel; pregna-4,20-dien-3-one $R_f$ 0.25).

Example 9

19-Norpregna-1,3,5(10),20-tetraen-3-ol, 9: Ethynylestradiol diacetate (2.0004 g, 5.2576 mmol) in 100 mL of anh. THF was added to approx. 140 mL of anh. $NH_3$ and sodium (1.88 g, 81.8 mg-atom) was added in small slivers over 5 min. After stirring the dark blue solution 1 h, abs. ethanol was added and the reaction was allowed to gradually warm to RT overnight. 100 mL of 1N HCl were added, the layers were separated, and the aqueous layer was extracted twice with 50 mL portions of ether. The combined organic phases were washed with 3 100 mL portions of brine, dried over magnesium sulfate, and filtered through diatomaceous earth. The residue was washed with 25 mL of ether and the combined filtrates were concentrated under reduced pressure. The residue was taken up in 25 mL of methylene chloride, dried over sodium sulfate, and filtered through diatomaceous earth. The residue was washed twice with 10 mL portions of methylene chloride and the combined filtrates were concentrated under reduced pressure. Flash chromatography (15% ethyl acetate/hexanes on silica gel) gave a white, crystalline solid with yellow spots (0.86 g, 3.0 mmol, 58%).

Example 10

19-Norpregna-1,3,5(10),20-tetraen-3-yl methyl ether, 10: To crude 19-Norpregna-1,3,5(10),20-tetraen-3-ol (9, 0.86g, 3.0 mmol) in 75 mL of 90% ethanol was added potassium carbonate (6.73 g, 55.2 mmol) and the suspension was refluxed ½ h. Dimethyl sulfate (0.75 mL) was added and the reaction was refluxed a further ½ h. Dimethyl sulfate was added in 3 1.8 mL aliquots (total=6.15 mL, 65.0 mmol) over 1 h, and reflux was continued for ½ h. Ice water (65 mL) was added and the mixture was cooled in an ice bath and stirred for 2h. The suspension was centrifuged and then filtered through a coarse frit. The residue was washed with 50 mL of water+50 mL of 5% sodium hydroxide+3 50 mL portions of water. The residue was recrystallized from aqueous ethanol to give fine white needles, m.p. 108.5°–110° C. (lit.m.p. 108°–110° C.).

Example 11

19-Norpregna-1,3,5(10),16-tetraen-6-on-20-yn-3-yl acetate, 11: Chromium trioxide (2.68 g, 2.68 mmol) was suspended in 40 mL of methylene chloride and the suspension was cooled in an ice-salt bath to −8° C. 3,5-Dimethylpyrazole (2.58 g, 26.8 mmol) was added and the suspension was stirred 20 min. 19-Norpregna-1, 3,5(10),16-tetraen-20-yn-3-yl acetate (0.86 g, 2.7 mmol) was added over 5 min., so that the reaction temperature did not exceed −7° C. After stirring an additional 2 h, the reaction mixture was poured through a 30 mm×116 mm column of silica gel and elution was continued under pressure with methylene chloride. Concentration of appropriate fractions gave a brown film (0.16 g, 0.48 mmol, 18%).

Example 12

19-Norpregna-1 3,5(10),16-tetraen-3 6β-diol-20-yne, 12: Crude 19-nonpregna-1,3,5(10),16-tetraen-6-on-20-yn-3-yl acetate (11, 0.16 g, 048 mmol) was suspended in 20 anh. ether, LAH (36.7 mg, 0967 mmol) was added, and the mixture was refluxed with exclusion of water for 18 h. After cooling, 1.22 g of Glauber's salt were added and the suspension was stirred ½ h. The mixture was filtered through diatomaceous earth and the residue was washed with 4 10 mL portions of hot ethyl acetate. Concentration of the combined filtrates, followed by purification by preparative TLC (50% ethyl acetate/hexanes on silica gel GF, 1000 μ) gave a white solid (26.0 mg, 88.3 μmol, 18%) homogeneous to TLC (50% ethyl acetate/hexanes on silica gel; $R_f$ 0.48).

Example 13

19-Norpreana-1,3,5(10),17-tetraen-3-ol, 13: Ethyltriphenylphosphonium bromice (1.3947 g, 3.7572 mmol) and potassium t-butoxide (422.5 mg, 3.765 mmol) suspended in anh. DMSO (4.1 mL) under argon were placed in an oil bath (80°–84° C.) and stirred 1 h. Equilin (200.2 mg, 0.7459 mmol) in 4.1 mL of anh. DMSO was added and the reaction was stirred a further hour. After cooling, 25 mL of ice-1N HCl was added and the mixture was extracted three times with 20 mL portions of ether. The combined organic extracts were washed with 25 mL of saturated sodium bicarbonate+ 25 mL of brine, dried over magnesium sulfate, and filtered through diatomaceous earth. The residue was washed with 10 mL of ether and the combined filtrates were concentrated under reduced pressure. Flash chromatography (20% ethyl acetate/hexanes on silica gel) followed by preparative TLC (20% ethyl acetate/hexanes on silica gel GF, 1000 μ) gave a slightly yellow resin (182.9 mg, 0.6523 mmol, 87%) homogeneous to TLC (20% ethyl acetate/hexanes $R_f$ 0.42).

Example 14

19-Norpregna-1,3,5(10),617-pentaen-3-ol, 14: Ethyltriphenylphosphonium bromide (1.3945 g, 3.7561 mmol) and potassium-butoxide (422.8 mg, 3.768 mmol) suspended in 4.1 mL of anh. DMSO under argon were placed in a 77°–79° C. bath and were stirred 1 h. 6-Dehydroestrone (200.4 mg, 0.7466 mmol) in 4.1 mL of anh. DMSO was added and the reaction was stirred in 1 h. The reaction mixture was allowed to cool and was then poured into 25 mL o fice-1N HCl. The mixture was extracted three times with 20 mL of ether and the combined organic extracts were washed with 25 mL of saturated sodium bicarbonate+25 mL of brine, dried over magnesium sulfate, and filtered through diatomaceous earth. The residue was washed with 10 mL of ether and the combined filtrates were concentrated under reduced pressure. Flash chromatography (15% ethyl acetate/hexanes) and preparative TLC (15% ethyl acetate/hexanes on silica gel GF, 1000 μ) gave an off-white crystalline solid (212.9 mg, >100%) homogeneous to TLC (15% ethyl acetate/ hexanes on silica gel, $R_f$ 0.21).

Example 15

19-Norpreana-1,3,5(10),6,8,17-hexaen-3-ol, 15: Ethyltriphenylphosphonium bromide (1.3945 g, 3.7561 mmol) and potassium t-butoxide (422.3 mg, 3.763 mmol) suspended in 4.1 mL of anh. DMSO under argon were placed in an oil bath (74°–83° C.) and the reaction was stirred 1 h. Equilenin (200.2 mg, 0.7518 mmol) in 4.1 mL of anh. DMSO was added and the reaction mixture was stirred a further hour. The mixture was poured into 25 mL of ice-1N HCl and extracted three times with 20 mL portions of ether. The combined organic extracts were washed with 25 mL of saturated sodium bicarbonate+25 mL of brine, dried over magnesium sulfate, and filtered through diatomaceous earth.

The residue was washed with 10 mL of ether and the combined filtrates were concentrated under reduced pressure. Flash chromatography (20% ethyl acetate/hexanes) and preparative TLC (20% ethyl acetate/hexanes on silica gel GF. 1000 μ) gave a light yellow, crystalline wax (180.6 mg, 0.6487 mmol, 86%) homogeneous to TLC.

Example 16

Electrophysioloaical Studies: The following electrophysiological studies were performed in clinically normal human volunteers of both sexes whose ages ranged from 19 to 29 years. No anesthetics were used, and female subjects were excluded if pregnant.

The stimulation and recording system consists of a "multifunctional miniprobe" described elsewhere (Monti-Bloch, L. and Grosser, B. L. (1991) "Effect of putative pheromones on the electrical activity of the human vomeronasal organ and olfactory epithelium." *J. Steroid Biochem. Molec. Biol.* 39:573582). The recording electrode is a 0.3 mm silver ball attached to a small (0.1 mm) silver wire insulated with Teflon@ the surface of the electrode is first treated to produce a silver chloride interface, and is then covered with gelatin It is positioned within a small caliber Teflon© catheter (dia=5 mm) such that the tip of the electrode protrudes approximately 2 mm. The Teflon© catheter is 10 cm in length and constitutes the terminal extension for a multichannel delivery system which delivers a continuous air stream carrying discreet pulses of chemosensory stimuli. The air stream first passes into a small chamber and is bubbled through a solution containing either a vomeropherin or an olfactant in a diluent or the diluent alone. A solenoid is used to rapidly redirect the air stream from the chamber to a route which bypasses the chamber. This creates a discreet pulse of stimulant in the air stream. A second, outer Teflon© tube with a diameter of 2 mm surrounds the catheter-electrode assemblage, and its central end is connected to an aspirator that provides continuous suction of 3 ml/s. This concentric arrangement of the outer suction tube allows the emitted chemosensory stimuli to be localized to an area we call a "minifield" (approx. dia=1 mm), and it avoids diffusion of substances either to the area outside the intended stimulation site or into the respiratory system. The entire stimulating and recording assemblage may be positioned either on the neurosensory epithelium within the VNo, or on the surface of the olfactory or respiratory epithelium.

Electro-vomeronasogram (EVG): Recordings are carried out in a quiet room with the subject supine; the multifunctional miniprobe is initially stabilized within the nasal cavity using a nasal retractor placed in the vestibule. Reference and ground electrodes consist of silver discs (8 mm), both of which are positioned on the glabella.

The entrance to the VNO, or vomeronasal pit, is identified by first dilating the nasal aperture and vestibule. A 6× magnifying binocular loupe with halogen illumination is then used to introduce the tip of the Teflon© catheter and recording electrode assemblage into the VNo opening where it is stabilized at an approximate depth of 1 mm within the vomeronasal passage. Optimal placement of the recording electrode is signaled after testing for an adequate depolarization in response to a test substance.

Electrical signals from the recording electrode are fed to a DC amplifier after which they are digitized, computer monitored, and stored. The peak-to-peak amplitude of the signals is measured, and the area under the depolarization wave is integrated, while continuously monitoring the signal both on the computer screen and on a digital oscilloscope. Artifacts produced by respiratory movements are deleted by training the subjects to practice mouth breathing with velopharyngeal closure. Samples of vomeropherins in concentration of 25–800 fmoles are delivered in the continuous air stream for durations from 300 milliseconds to 1 second. Usually, intervals of 3 to 5 minutes separated each series of short test pulses. All components of the lines carrying the test stimuli are made of Teflon©, glass or stainless steel and are carefully cleaned and sterilized before each use. Activity was recorded using standard electroencephalographic (EEG) electrodes placed at positions Cz-A1 and Tz-A1 of the international 10120 system; the ground electrode was placed on the mastoid process. Skin temperature (ST) was recorded by a small (1.0 mm) thermistor probe placed in the right ear lobe. Respiratory frequency (RF) was measured with an adjustable strain gauge placed around the lower thorax. All electrical signals were DC amplified, digitized (MP-100, Biopac systems) and continuously monitored utilizing a computer.

Statistical Analysis: EVGs, peak-to-peak changes and frequency changes of other parameters were measured and statistically analyzed. The significance of the results was determined by either using paired t-tests or analysis of variance (ANOVA).

Reflex Effects of Vomeropherins: Studies were conducted to determine the central nervous system (CNS) reflex responses to vomeropherin stimulation of the VNO. The sexually dimorphic local responses induced by vomeropherins were sometimes mirrored in the autonomic response of male & female subjects.

Cortical activity was recorded from Cz and Tz in male and female subjects during application to the VNO of air pulses (300 ms to 1 sec) containing 200 fmoles of vomeropherin. There is also preliminary evidence that the EVG is not associated with trigeminal nociceptor endings since application of a local anesthetic (2% lidocaine) to the respiratory epithelium of the nasal septum neither blocks nor diminishes the EVG (Monti-Bloch, L. and Grosser, B. L. (1991) "Effect of putative pheromones on the electrical activity of the human vomeronasal organ and olfactory epithelium." *J. Steroid Biochem.* Molec. Biol. 39:573–582.), also, subjects failed to report sensations of pain as a consequence of any of the stimulation procedures.

The following study compares the effect of 23 vomeropherins with 19-norpregnane structure, and placebo (propylene glycol), on autonomic activity and EEG. Twelve healthy human subjects (6 women and 6 men), ages 19 to 29 participated in this study. All substances were delivered airborne to the vomeronasal organ (VNO) puff lasting 5 seconds. For this purpose we use a miniprobe electrode described elsewhere, that allowed local stimulation and simultaneous recording of the organ's electrovomerogram (EVG). The parameters recorded were: electrodermal activity (EDA), respiratory frequency (RF), electrocardiogram (CF), electromyogram (EMG), body temperature (BT), and EEG from CzAl and T3A1. Autonomic activity, EEG and EVG were recorded using surface electrodes. All the techniques used were non invasive. The procedure was done in two recording sessions each lasting one hour. The electrical recordings were amplified, dignitized, and monitored and stored in a computer. Processing and analysis of the results were done offline.

The data on the tests on the women is shown in FIGS. 3–24, and the data on the men is shown in FIGS. 25–46.

The results were summarized in the following tables showing the overall effect of each vomeropherin already subtracted from control. An arbitrary score from 0 to 5 was assigned to compare the activity of the compounds relative to each other, but virtually all of the compounds tested had some effect.

These results show that the effect of some vomeropherins on autonomic activity and EEG is significantly different from placebo. Also shown is that some substances do not have significantly different effects in both genders.

| SUMMARY OF EFFECTS OF 19-NOR PREGNANE VOMEROPHERINS ON EEG AND AUTONOMIC ACTIVITY IN WOMEN. n = 6 | | | | | | | | | | |
|---|---|---|---|---|---|---|---|---|---|---|
| | EVG | EDA | RF | CF | EMG | BT | $\alpha$-CA | $\beta$CA | PERFORMANCE | SCORE |
| METHOL ETHER OF E2/P8 | +25 | +100 | −5 | −5 | 0 | −2.5 | −10 | −35 | EDA+, RF−, CF−, $\beta$− | 5 |
| E9/P2 | +5 | −10 | −2.5 | +10 | +5 | −2.5 | +5 | −35 | CF+, $\alpha$+, $\beta$− | 3 |
| E4/P2 | +2.5 | −10 | −2 | +5 | −5 | 0 | +2.5 | −2.5 | EDA−, EMG− | 3 |
| E7/P1 | +30 | +70 | −5 | −5 | 0 | 0 | −5 | −2 | EDA+RF−CF− | 4 |
| ACETATE OF E2/P8 | +50 | +130 | 0 | 0 | 0 | +6 | 0 | −15 | EDA+, BT+, $\beta$− | 4 |
| E3/P1 | +20 | +70 | −2.5 | −2.5 | 0 | +3 | −10 | −30 | EDA+ | 2 |
| E10/P2 | +3 | −10 | 0 | +10 | −5 | 0 | +10 | +10 | EDA−, CF+EMG−, $\alpha$+ | 5 |
| E2/P7 | +25 | +50 | +5 | −5 | 0 | +10 | −15 | −30 | EDA+, BT+ | 3 |
| E2/P5 | +25 | +30 | 0 | 0 | 0 | 0 | −10 | −40 | 0 | 0 |
| E2/P6 | +20 | +50 | 0 | −5 | 0 | 0 | −15 | −30 | EDA, CF− | 3 |
| E1/P1 | +45 | +110 | +5 | 0 | 0 | 0 | −5 | −10 | 0 | 0 |
| E2/P1 | +40 | +95 | +3 | +5 | 0 | 0 | 0 | −15 | EDA+, RF+, CF+ | 4 |
| METHOL ETHER OF E2/P1 | +20 | +85 | −2.5 | −5 | 0 | 0 | −6 | −20 | EDA+, CF− | 3 |
| E13/P1 | +1 | −10 | 0 | 0 | −5 | 0 | 0 | −40 | EDA−, EMG−, $\beta$− | 4 |
| E11/P1 | +20 | −10 | 0 | +5 | −2.5 | −1 | 0 | −25 | 0 | 0 |
| E5/P1 | 0 | −10 | 0 | 0 | 0 | 0 | 0 | −40 | 0 | 0 |
| ACETATE OF | +2.5 | −10 | −2.5 | +2.5 | −5 | −3 | +10 | −20 | EMG−, BT−, $\alpha$+, $\beta$− | 5 |
| E2/P8 | +25 | +110 | 0 | 0 | 0 | +10 | +7 | −20 | EDA+, BT+, $\alpha$+, $\beta$+ | 5 |
| E2/P2 | +20 | +20 | −2.5 | −5 | 0 | −2.5 | +7 | −25 | CF−, BT−, $\alpha$+, $\beta$− | 5 |
| E2/P4 | +50 | +110 | +2.5 | 0 | 0 | 0 | +30 | −10 | EDA+, $\alpha$+, $\beta$− | 4 |
| E12/P8 | +35 | +100 | 0 | −5 | 0 | −3 | −10 | −25 | EDA+, CF−, BT− | 4 |
| E8/P1 | +35 | +105 | +2.5 | 0 | 0 | −1 | −10 | −40 | 0 | 0 |

| SUMMARY OF EFFECTS OF 19-NOR PREGNANE VOMEROPHERINS ON EEG AND AUTONOMIC ACTIVITY IN MEN. n = 6 | | | | | | | | | | |
|---|---|---|---|---|---|---|---|---|---|---|
| | EVG | EDA | RF | CF | EMG | BT | $\alpha$-CA | $\beta$CA | PERFORMANCE | SCORE |
| METHOL ETHER OF E2/P8 | +12 | +95 | 0 | −5 | −2.5 | −2.5 | +2.5 | −10 | EDA+, CF−, | 3(+) |
| E9/P2 | +20 | −20 | 0 | +2.5 | −2.5 | −5 | −7 | +40 | BT− | 2 |
| E4/P2 | +15 | −20 | 0 | +2.5 | 0 | −2.5 | −2.5 | −20 | 0 | 0 |
| E7/P1 | +18 | +70 | 0 | 0 | 0 | +7 | −2.5 | −30 | EDA+, BT+$\alpha$− | |
| ACETATE OF E2/P8 | +40 | +80 | 0 | 0 | 0 | +2.5 | −10 | −20 | EDA+ | 2 |
| E3/P1 | +15 | +50 | 0 | +2.5 | 0 | −5 | −10 | −30 | EDA+, BT−, $\beta$+ | 4 |
| E10/P2 | +20 | −20 | 0 | +2.5 | −2.5 | −1 | 0 | +40 | 0 | 0 |
| E2/P7 | +30 | +120 | 0 | +2.5 | 0 | 0 | −10 | −20 | 0 | 0 |
| E2/P5 | +10 | +90 | 0 | 0 | 0 | +10 | −5 | −30 | EDA+, BT+, $\beta$− | 4 |
| E2/P6 | +12 | +100 | 0 | 0 | 0 | −2.5 | 0 | −20 | EDA+ | 2 |
| E1/P1 | +35 | +120 | −2.5 | 0 | 0 | +2.5 | −2.5 | −20 | EDA+ | 2 |
| E2/P1 | +30 | +120 | 0 | 0 | 0 | −7 | −10 | −20 | EDA+, BT−, (EEG±) | 4 |
| METHOL OF E2/P1 | +15 | +110 | −5 | 0 | 0 | 0 | 0 | −20 | EDA+, RF− | 3 |
| E13/P1 | +20 | −20 | 0 | 0 | −2.5 | 0 | −5 | −15 | 0 | 0 |
| E11/P1 | +18 | −20 | +2.5 | 0 | 0 | −2.5 | −5 | −15 | 0 | 0 |
| E5/P1 | +10 | −20 | 0 | −2.5 | −2.5 | 0 | −5 | −10 | 0 | 0 |
| ACETATE OF E6/P8 | +2.5 | −20 | 0 | −2.5 | −2.5 | −2.5 | −5 | −15 | 0 | 0 |
| E2/P8 | +30 | +100 | 0 | 0 | 0 | 0 | −10 | −20 | 0 | 0 |
| E2/P2 | +15 | +80 | 0 | 0 | 0 | +2.5 | −5 | −25 | 0 | 0 |
| E2/P4 | +30 | +80 | −2.5 | 0 | 0 | −5 | −10 | −20 | EDA+, BT−, (EEG±) | |
| E12/P8 | +25 | +120 | 0 | 0 | 0 | +2.5 | −10 | −25 | EDA+ | 2 |
| E8/P1 | +30 | +130 | 0 | 0 | 0 | +2.5 | −5 | −20 | EDA+ | 2 |

What is claimed is:

1. A pharmaceutical composition suitable for nasal administration in an individual, said composition comprising a vomeronasal organ-stimulating effective amount of a 19-norpregnane steroid or mixture of 19-norpregnane steroids and a pharmaceutically acceptable carrier, wherein said steroid has the formula:

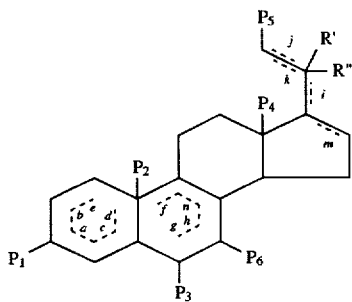

wherein $P_1$ is oxo, α- or β-hydroxy, α- or β-acetoxy, α- or β-propionoxy, α- or β-lower alkoxy, α- or β-lower acyloxy or α- or β-benzyloxy;

"a", "b", "c", "d", "e", "f", "g", "h", "i", "j", "m" and "n" are alternative sites for optional double bonds, and "k" may be absent or present with "j" to form a triple bond;

$P_2$ is a hydroxy, hydrogen, lower alkoxy of 1 to 6 carbon atoms, or $P_2$ is absent;

$P_3$ is oxo, hydrogen, hydroxy, lower alkoxy of 1–6 carbon atoms or halo;

$P_4$ is methyl or ethyl;

$P_5$ is hydrogen, methyl or halo;

$P_6$ is hydrogen or methyl;

R' and R" are independently, hydrogen or halo, or are absent.

2. A composition according to claim 1 wherein "a", "e" and "d" are doubled bonds.

3. The pharmaceutical composition according to claims 1 or 2 wherein said steroid is dissolved in said carrier.

4. The pharmaceutical composition according to claims 1 or 2 wherein said composition is in a liquid form.

5. The pharmaceutical composition according to claims 1 or 2 wherein said composition further contains a pharmaceutically acceptable ointment base.

6. The pharmaceutical composition according to claims 1 or 2 which contains no more than one of said steroids.

7. The pharmaceutical composition according to claims 1 or 2 which contains more than one of said steroids.

8. A composition according to claim 1 comprising 19-norpregna-1,3,5(10)-trien-3-ol.

* * * * *